US012216096B1

(12) United States Patent
Jeske

(10) Patent No.: US 12,216,096 B1
(45) Date of Patent: Feb. 4, 2025

(54) SYSTEMS AND METHODS FOR PLOTTING SOIL PROFILE DENSITY WITH HANDHELD PENETROMETERS

(71) Applicant: TERRAFORM TILLAGE LLC, Eldora, IA (US)

(72) Inventor: Joshua Jeffrey Dallas Jeske, Eldora, IA (US)

(73) Assignee: Terraform Tillage LLC, Eldora, IA (US)

( * ) Notice: Subject to any disclaimer, the term of this patent is extended or adjusted under 35 U.S.C. 154(b) by 0 days.

(21) Appl. No.: 18/738,580

(22) Filed: Jun. 10, 2024

Related U.S. Application Data

(60) Provisional application No. 63/471,900, filed on Jun. 8, 2023.

(51) Int. Cl.
*G01N 3/42* (2006.01)
*G01N 3/06* (2006.01)
(Continued)

(52) U.S. Cl.
CPC ............ *G01N 3/42* (2013.01); *G01N 3/06* (2013.01); *G01N 33/24* (2013.01); *G06Q 50/02* (2013.01)

(58) Field of Classification Search
CPC .......... G01N 3/40; G01N 33/24; G01N 33/12; G01N 33/18; G01N 29/12; G01N 17/00;
(Continued)

(56) References Cited

U.S. PATENT DOCUMENTS

| 9,809,934 B2 * | 11/2017 | Gourves | H04N 23/00 |
| 2007/0131025 A1 * | 6/2007 | Kinast | G01N 33/24 |
| | | | 73/84 |

(Continued)

FOREIGN PATENT DOCUMENTS

| BR | PI0802918 A2 | 7/2009 |
| BR | PI0905016 A2 | 11/2010 |

OTHER PUBLICATIONS

"Soil Compaction Meters" (Online product listing) Fieldscout SC 900 Meter, Spectrum Soil Compaction Meter, Soil Compaction Meter. https://www.specmeters.com/soil-and-water/soil-compaction/. Dec. 5, 2011. Retrieved from Internet Archive Wayback Machine https://web.archive.org/web/20111205005600/https://www.specmeters.com/soil-and-water/soil-compaction/.

(Continued)

*Primary Examiner* — Brandi N Hopkins
(74) *Attorney, Agent, or Firm* — Nyemaster Goode P.C.

(57) ABSTRACT

A penetrometer system having a handheld, manually implemented penetrometer that includes a downwardly extending central support pole having a top portion, a bottom, and a ground engaging end opposite the top portion at an end distal from the top portion and a top end opposite the ground engaging end; an outwardly extending right side handle engaged with the top portion; an outwardly extending left side handle engaged with the top portion; a pressure gauge having a perimeter defining a gauge perimeter shape wherein the pressure gauge has a pressure sensor system; and a mounting system for the removable attachment of a mobile computing device such that the mobile computing device is in line or at least substantially in line with the downwardly extending central support pole and a display screen of the mobile computing device is viewable while the penetrometer is in use by the user.

20 Claims, 17 Drawing Sheets

(51) Int. Cl.
*G01N 33/24* (2006.01)
*G06Q 50/02* (2012.01)

(58) Field of Classification Search
CPC .......... G01N 3/32; G01N 29/14; G01N 30/02; G01N 33/0049; G01L 19/086; G01L 17/00; G01L 19/08; G01L 27/00; G01B 21/18; G01B 13/10; G01M 3/26; G07C 5/0808
See application file for complete search history.

(56) References Cited

U.S. PATENT DOCUMENTS

| | | | |
|---|---|---|---|
| 2011/0226044 A1* | 9/2011 | Hughes | G01N 3/42 73/54.02 |
| 2014/0116162 A1* | 5/2014 | Christian | G01B 5/30 73/866 |

OTHER PUBLICATIONS

"PenetroLOG" (Online product page) https://www.falker.com.br/en/penetrolog. Nov. 9, 2022. Retrieved on Internet Archive Wayback Machine https://web.archive.org/web/20221109154224/https://www.falker.com.br/en/penetrolog on Jun. 8, 2024.

"Soil Compaction Tester" (Online product page) https://dickey-john.com/products/accessories/soil-compaction-tester/soil-compaction-testing/, Feb. 2, 2023. Retrieved on Internet Archive Wayback Machine https://web.archive.org/web/20230202215418/https://dickey-john.com/products/accessories/soil-compaction-tester/soil-compaction-testing/ on Jun. 8, 2024.

"SpotOn® Digital Soil Compaction Meter" (online product page) https://innoquestinc.com/product/spoton-digital-compaction-meter/. Sep. 26, 2020, retrieved from Internet Archive Wayback Machine https://web.archive.org/web/20200926084337/https://innoquestinc.com/product/spoton-digital-compaction-meter/ on Jun. 8, 2024.

* cited by examiner

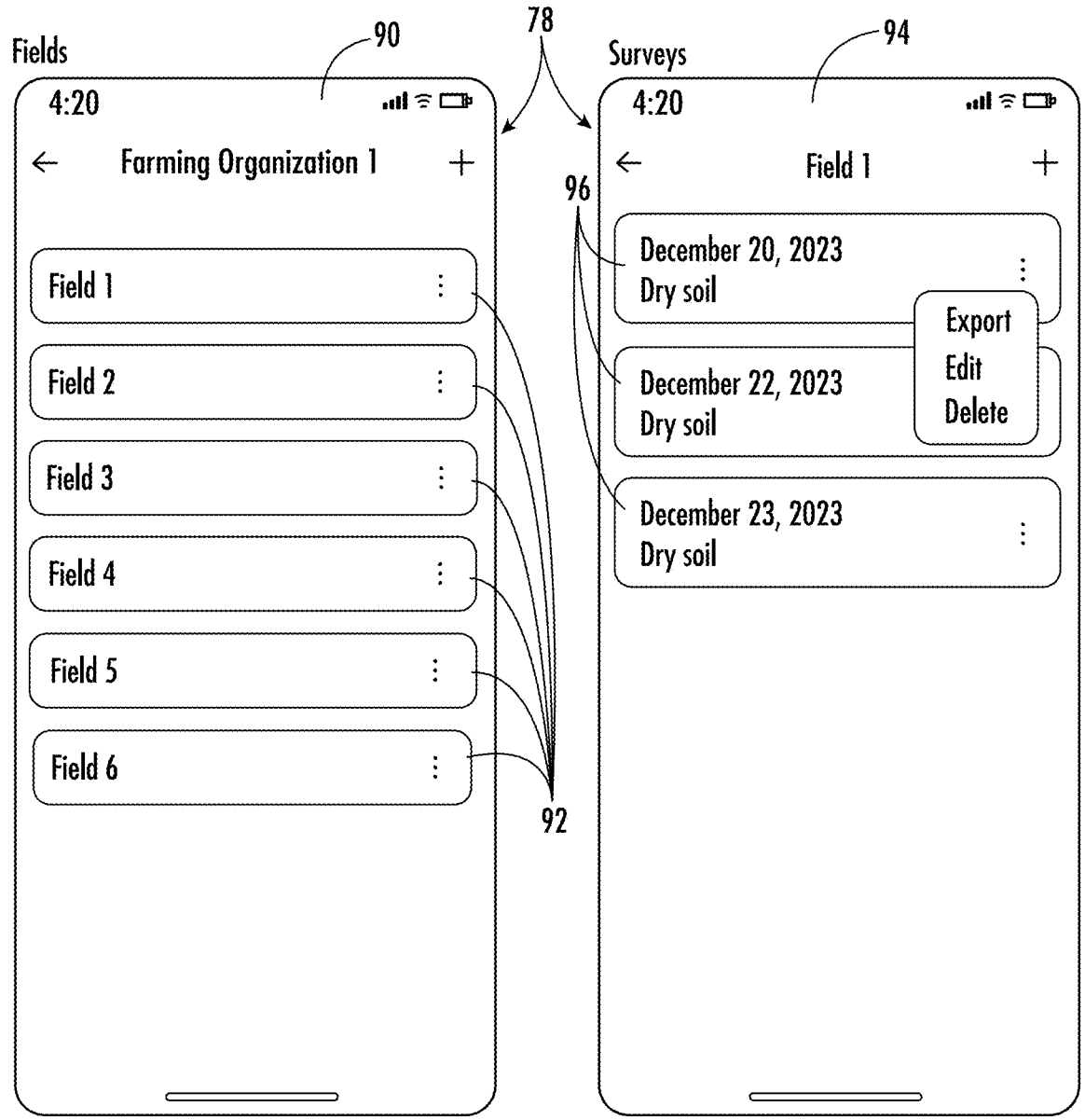

SYSTEMS AND METHODS FOR PLOTTING SOIL PROFILE DENSITY WITH HANDHELD PENETROMETERS

CROSS-REFERENCE TO RELATED APPLICATION

This application claims priority to U.S. Provisional Ser. No. 63/471,900, filed on Jun. 8, 2023, entitled "SYSTEMS AND METHODS FOR PLOTTING SOIL PROFILE DENSITY WITH HAND HELD PENETROMETERS", the disclosure of which is hereby incorporated herein by reference in its entirety.

BACKGROUND

Crop yield can be affected by variations in soil density across a crop field. Typically, farmers will till an entire field uniformly, even if one section is more or less compacted than another. However, this can lead to over tilling, which, in turn, causes negative environmental effects such as increased erosion, pollution, and nutrient leaching. Penetrometers, or soil compaction probes, can be useful tools for finding the variations of soil density around a given field.

SUMMARY

An aspect of the present disclosure is generally directed to a soil penetrometer system made up of a handheld, manually implemented penetrometer and a mobile computing application that is used in conjunction with a mobile computing device such as a smart phone. The handheld, manually implemented penetrometer that includes a downwardly extending central support pole having a top portion, a bottom, and a ground engaging end opposite the top portion at an end distal from the top portion and a top end opposite the ground engaging end. Engaged with the top portion is an outwardly extending right side handle and an outwardly extending left side handle as well as a pressure gauge. The pressure gauge has a perimeter defining a gauge perimeter shape. The pressure gauge has a pressure sensor system chosen from either a fluid pressure dial or a load cell force measurement system. In the fluid pressure dial there is a downwardly extending central support pole engaging location on a central pole facing surface of the pressure gauge that engages the top end of the downwardly extending central support pole when the penetrometer is in use. The force applied by the downwardly extending central support pole to the downwardly extending central support pole engaging location and the pressure on the downwardly extending central support pole engaging location is displayed to the user on a display on a top, user-facing surface of the pressure gauge. With the load cell force measurement system, there is a load cell with the top portion of the downwardly extending central support pole that converts pressure applied by the downwardly extending central support pole to the load cell into electrical current that correlates to a pressure level. The pressure level is displayed to a user on a display on a top, user-facing surface of the pressure gauge. The pressure gauge is positioned directly over the downwardly extending central support pole and above the right side handle and a portion of the left side handle. Also included is a mounting system for the removable attachment of a mobile computing device such that the mobile computing device is in line or at least substantially in line with the downwardly extending central support pole. The display screen of the mobile computing device is viewable while the penetrometer is in use. The mounting system includes a gauge perimeter shape engaging clamping section where most, or all, of the gauge perimeter shape engaging clamping section has an overall shape that is the same shape or substantially the same shape as the gauge perimeter shape. The clamping section is frictionally held in engagement with the perimeter of the pressure gauge using a clamp. The clamp may be secured with a fastener or fastener system such as a nut and bolt fastener. The clamp or fastener may be loosened or removed by hand and without the use of tools to disengage the mounting clamp system from the perimeter of the pressure gauge when desired by the user. The mounting clamp system further comprises a mobile computing device retention portion that releasably engages and disengages a mobile computing device.

Another aspect of the present disclosure generally includes a method for performing a soil compaction survey for a geographical area to determine a level of compaction in at least one predetermined depth at a plurality of points within the geographical area. The method includes the following steps. The first step is inserting a handheld penetrometer to a predetermined depth at a point within the geographical area. The penetrometer is hand operated without the use of tools. It includes a downwardly extending central support pole having a top portion with a top end, and a ground engaging end that is opposite from the top end on the downwardly extending support pole. The penetrometer has an outwardly extending right side handle and outwardly extending left side handle engaged to the downwardly extending support pole. There is also a pressure gauge having a perimeter defining a gauge perimeter shape. The pressure gauge has a pressure sensor system that detects a pressure exerted on the downwardly extending support pole and the pressure exerted on the downwardly extending support pole is displayed on a top, user facing surface of the pressure gauge and the pressure gauge presents a level of compaction at the predetermined depth at a point within the geographical area as a pressure reading. The second step of the method is manually or automatically recording a pressure reading displayed by the pressure gauge of a first predetermined depth at the point within the geographical area into a soil compaction mapping and tracking system. The soil compaction mapping and tracking system displays a map of the geographical area and a location of a user of the handheld penetrometer on the map of the geographical area in real time. The pressure reading corresponds to a point on the map of the geographical area and can be viewed by one or more users of the soil compaction mapping and tracking system in real time by selection of the point on the map of the geographical area. The soil compaction mapping and tracking system is held on a computing device. In another step, the penetrometer may be optionally inserted into an optional additional predetermined depth at the point within the geographical area. Then, optionally manually or automatically recording a pressure reading displayed by the pressure gauge of the optional additional predetermined depth at a point within the geographical area into the soil compaction mapping and tracking system is done by the soil compaction mapping and tracking system. The pressure reading corresponds to the point on the map of the geographical area and can be viewed by the one or more users of the soil compaction mapping and tracking system in real time by selection of the point on the map of the geographical area. The optional steps are repeated for any number of additional depths, and then the user may move the penetrometer to other points within the geographic area and the measuring steps are repeated at each new point.

Yet another aspect of the present disclosure is generally directed to a method for performing a soil compaction survey for a geographical area to determine a level of compaction in at least one depth at a plurality of points within the geographical area. The method typically includes the step of inserting a handheld penetrometer at a constant rate into a point within the geographical area. The penetrometer is typically hand operated without the use of tools, and includes a downwardly extending support pole having a top portion with a top end, and a ground engaging end that is opposite from the top end on the downwardly extending support pole. There is also an outwardly extending right side handle engaged to the downwardly extending support pole and an outwardly extending left side handle engaged to the downwardly extending support pole. There is a pressure gauge having a perimeter defining a gauge perimeter shape and the pressure gauge has a pressure sensor system that detects a pressure exerted on the downwardly extending support pole. The pressure exerted on the downwardly extending support pole is displayed on a top, user facing surface of the pressure gauge. The pressure gauge presents a level of compaction at a predetermined depth at a point within the geographical area as a pressure reading. Then a pressure reading displayed by the pressure gauge of a first predetermined depth at the point within the geographical area into a soil compaction mapping and tracking system is recorded using a user operated mobile computing device. The soil compaction mapping and tracking system displays a map of the geographical area and a location of a user of the handheld penetrometer on the map of the geographical area in real time, and the pressure reading corresponds to a point on the map of the geographical area and can be viewed by one or more users of the soil compaction mapping and tracking system in real time by selection of the point on the map of the geographical area. The soil compaction mapping and tracking system is held on the user operated mobile computing device. The penetrometer may be optionally inserted to any number of additional optional depths at a constant rate where the penetrometer reads pressure and records soil compaction based on the pressure at all depths as the penetrometer travels through the ground. The pressure readings are typically automatically recorded from the pressure gauge for any number of optional additional predetermined depths at a point within the geographical area into the soil compaction mapping and tracking system. The pressure reading corresponds to the point on the map of the geographical area and can be viewed by the one or more users of the soil compaction mapping and tracking system in real time by selection of the point on the map of the geographical area. The steps may be repeated at a given location or proximate a given location. The penetrometer may then be moved to a subsequent point/geographic location in the field and the measuring process repeated. This may be done until an accurate graphical and statistical measurement and/or estimate of the soil compaction of the a given field is obtained.

BRIEF DESCRIPTION OF THE DRAWINGS

In the drawings:

FIG. 11 is a graphical user interface of a field selection screen of a mobile computing application according to an aspect of the present disclosure.

FIG. 12 is a graphical user interface of a survey selection screen of a mobile computing application according to an aspect of the present disclosure.

DETAILED DESCRIPTION OF EMBODIMENTS

Figure 2:
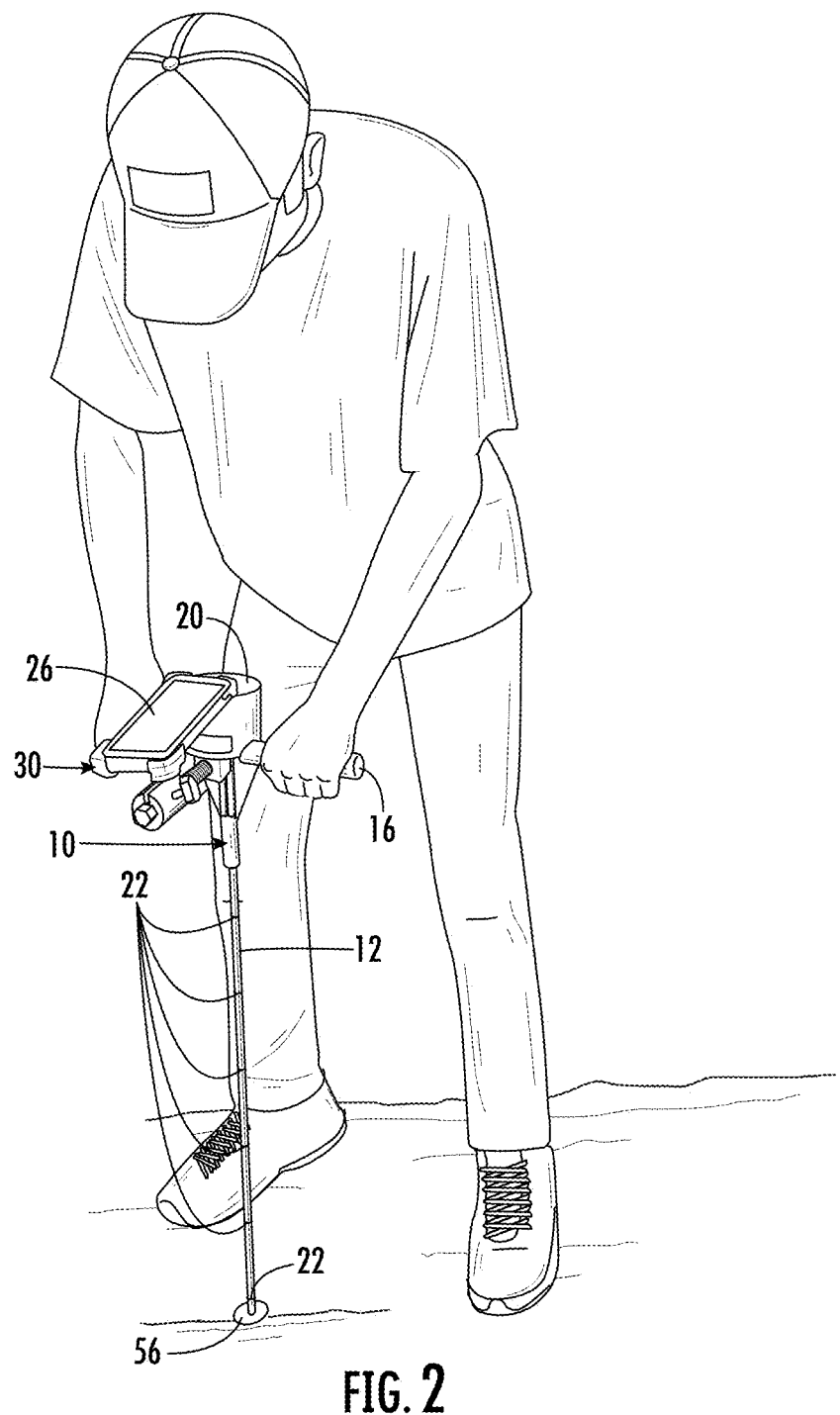
FIG. 2 is perspective view of a user operating the phone integrating penetrometer according to an aspect of the present disclosure.

For purposes of description herein, the terms "upper," "lower," "right," "left," "rear," "front," "vertical," "horizontal," and derivatives thereof shall relate to the invention as oriented as one would use/face the penetrometer as shown in FIG. 2. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure and claimed invention, and further it is to be understood that such concepts are intended to be covered by the following claims unless these claims by their language expressly state otherwise.

It is to be understood that the disclosed innovations may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. Where a range of values is provided, it is understood that each intervening value, to the tenth of the unit of the lower limit unless the context clearly dictates otherwise, between the upper and lower limit of that range, and any other stated or intervening value in that stated range, is encompassed within the scope of the present disclosure. The upper and lower limits of these smaller ranges may independently be included in the smaller ranges, and are also encompassed within the scope of the present disclosure, subject to any specifically excluded limit in the stated range. Where the stated range includes one or both of the limits, ranges excluding either or both of those included limits are also included in the scope of the present disclosure. All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all sub-ranges beginning with a minimum value of 1 or more and ending with a maximum value of 10 or less (e.g., 1 to 6.1, or 2.3 to 9.4), and to each integer (1, 2, 3, 4, 5, 6, 7, 8, 9, 10) contained within the range. In this specification and the appended claims, the singular forms "a," "an" and "the" include plural reference unless the context clearly dictates otherwise. All combinations of method steps or process steps as used herein can be performed in any order, unless otherwise specified or clearly implied to the contrary by the context in which the referenced combination is made.

To the extent that the terms "includes" or "including" or "have" or "having" are used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A" or "B" or both "A" and "B". When the Applicant intends to indicate "only A or B but not both" then the term "only A or B but not both" or similar structure will be employed. Thus, use of the term "or" herein is the inclusive, and not the exclusive use. Also, to the extent that the terms "in" or "into" are used in the specification or the claims, it is intended to additionally mean "on" or "onto." In this specification and the appended claims, the singular forms "a," "an" and "the" include plural reference unless the context clearly dictates otherwise.

Figure 1:
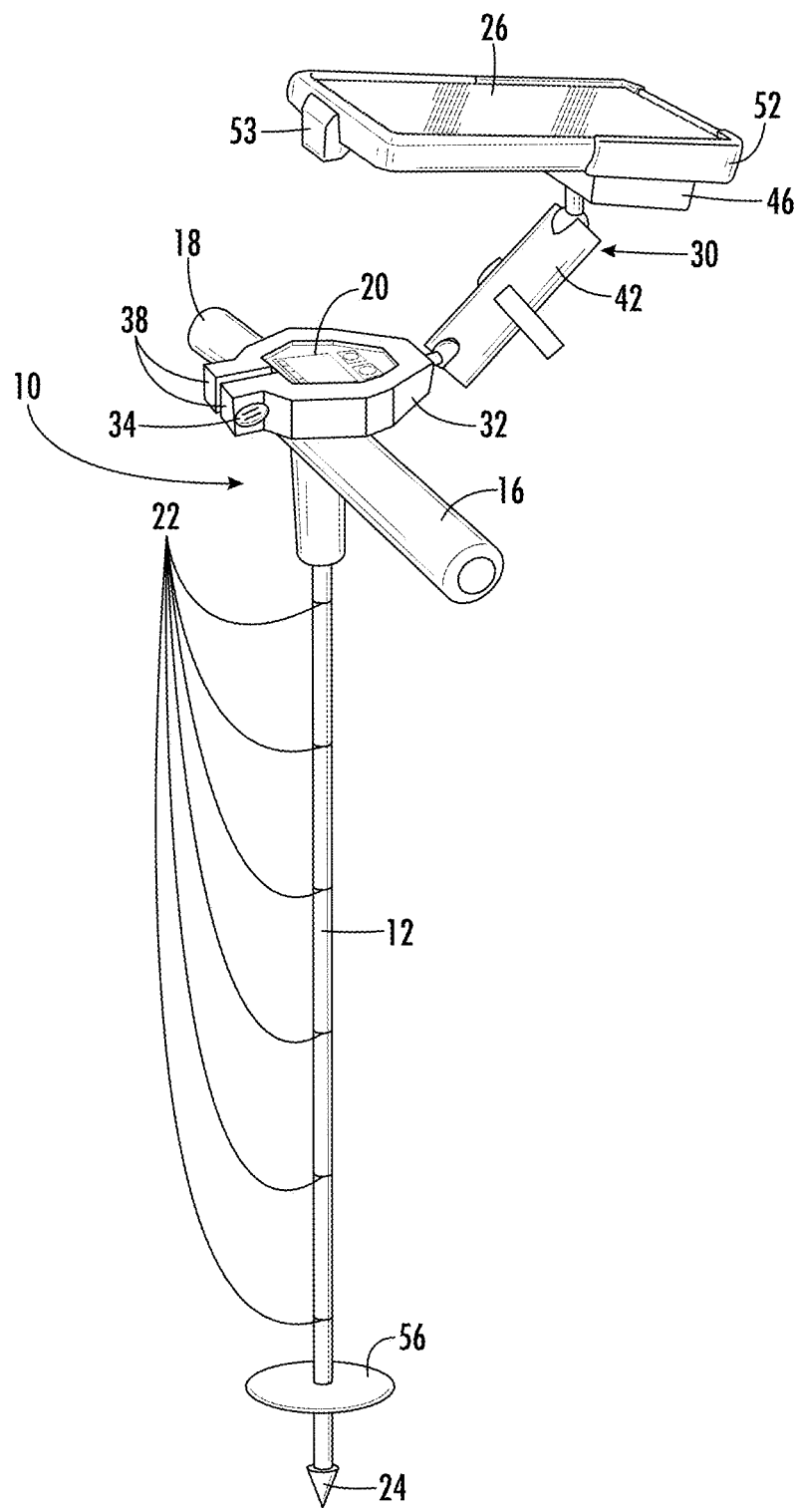
FIG. 1 is a perspective view of the phone integrating penetrometer according to an aspect of the present disclosure.

Referring to FIGS. 1-2, a penetrometer 10 used in various aspects of the present disclosure typically has a support rod 12, a left side handle 16, a right side handle 18, an intersection between the right side handle 18 and the left side handle 16 and attached to an end of the support rod 12, a pressure gauge 20 located near the intersection on the end of the support rod 12. The pressure gauge is typically above the intersection, but may alternatively be elsewhere along the support pole. The support rod 12 typically has a plurality of notches 22 typically evenly spaced along the support rod 12, and a cone 24 located on an opposite end of the support rod 12 from the intersection and the pressure gauge 20. The cone 24, facilitates the insertion of the penetrometer 10 into the soil and keeps the leveling plate 56 from falling off the bottom of the support rod 12 during use. The right side handle 18 and the left side handle 16 are typically located in the same horizontal plane as one another and extend in opposite directions to one another. The handles are both typically at an angle of about 90 or exactly 90 degrees with the support rod 12 of a sufficient strength so that a human can put their weight on them to insert the penetrometer 10 into the ground. Both of the handles are correctly sized as to allow a human user to grasp them with their hands and allow easy manipulation of the penetrometer 10. The support rod 12 typically includes a plurality of notches 22, which are typically evenly spaced, but can be randomly spaced, located along its entire height. The notches 22 are typically spaced around three inches apart or four inches apart and are used to indicate the depth of the support rod 12 under the soil surface for accurate measurements. However, the notches 22 could potentially be spaced in any configuration that is convenient and useful to the user.

Figure 8:
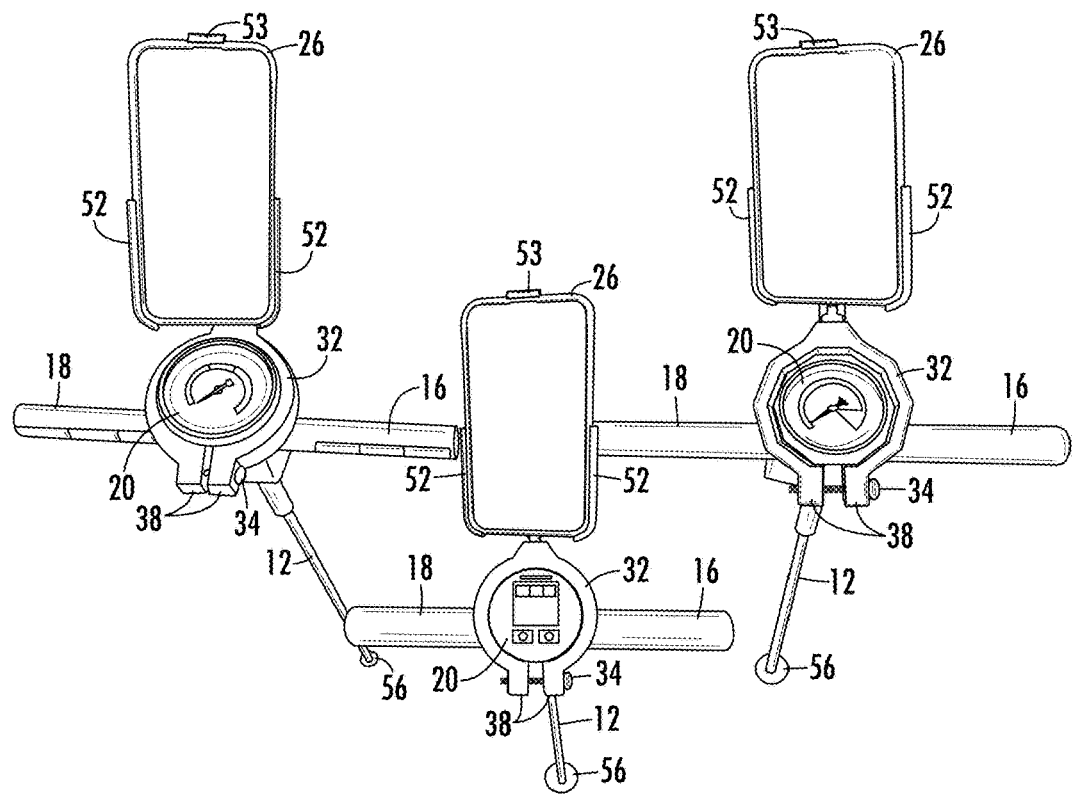
FIG. 8 is an upper perspective view of three penetrometers with varying designs for their ring clamps according to an aspect of the present disclosure. The ring clamps are different to attach to multiple forms of penetrometer. In this case, a circular ring clamp for a penetrometer on the left, a hexagonal ring clamp for the penetrometer on the right, and a smaller circular ring clamp to attach to the INNOQUEST®, SPOTON® Digital Soil Compaction Meter in the center that also may be attached to an AGIMATE® Soil Compaction Tester.

To determine the depth, the user pushes the penetrometer 10 downward into the soil until a notch 22 that indicates the desired soil depth lines up with the soil surface and/or a leveling plate resting on the soil surface. The pressure gauge 20 is attached to the penetrometer 10 at a point just above the intersection of the handles and the support rod 12. The pressure gauge 20 may include a textured covering, such as a knurling texture, and may facilitate the frictional attachment of a ring clasp (FIG. 8). The cover may be made of a hard rubber or plastic, but theoretically any sufficiently rigid material that can protect the meter could be used. A user should be able to face downward and easily view the pressure gauge 20 while they are using the penetrometer 10. The pressure gauge 20 will typically give the penetration resistance of the soil in units of psi. Alternatively, the pressure gauge 20 may use units such as Kilopascal (Kpa) or Kilopound Force per square inch (Kpsi). The measured pressure together with the measured depth of the support rod 12 will allow for the calculation of the soil density at different depths below the soil surface. A user should insert the penetrometer 10 into the soil at a rate of about one inch per second. The pressure gauge 20 is typically centered on the overall penetrometer.

The penetrometer uses a pressure sensor system to measure soil compaction readings. The readings are then displayed on the pressure gauge. The pressure sensor system may be a direct force measurement system that engages the support pole. When the support pole is inserted into the soil, the surrounding soil presses against the support pole and thereby exerts a force on the direct force measurement system. The sensor may be a strain gauge, which measures the contraction of a spring element within the penetrometer pressure sensor system. The sensor may be a piezoelectric sensor that measures the force by a change in charge, or a capacitive sensor that measures the capacitance between two plates that are brought together as pressure is exerted on the support pole. The sensor may also be a fluid pressure sensor. The sensor may also be a pressure transducer or a pressure transmitter.

While the penetrometer 10 may be primarily intended for use in crop fields, it can be used in other applications. Testing compaction in orchards or in forestry are both useful endeavors for penetrometers, as soil compaction can affect trees similarly to field crops. Overly compacted soil is a common killer of even large trees. The penetrometer 10 can also be used in personal gardens of any size. Any situation where soil compaction will affect plant growth is a potential use case for the penetrometer 10. Measuring soil compaction is useful even outside crop growth. The penetrometer system of the present disclosure could also be used to determine the effectiveness of swales or other water guiding land features.

In another aspect of the disclosure a penetrometer kit 28 (FIG. 3) may utilize a mobile computing device attachment 30 to adapt a mobile computing device 26 such as a "smart" phone 26 to the penetrometer 10 of the present disclosure, a leveling plate 56, and a monitor bar adapter 60 to attach a mobile computing device holder 46 to the inside of a vehicle, typically a tractor or other farming vehicle especially one used in tilling or seeding. The smart phone of the present disclosure is one type of mobile computing device that may be employed. For purposes of the present disclosure, the term "mobile computing device" is meant to include mobile phones (frequently referred to as smartphones) as well as other general purpose or application specific computing devices that may lack the phone functionality, such as portable media players, cameras, and global positioning system (GPS) devices. Skilled artisans will immediately recognize that certain mobile computing devices, such as IPADS, IPHONES® and IPOD TOUCH® devices developed by and available from Apple Corporation of Cupertino, Calif., as well as any one of a wide variety of devices based on the ANDROID® operating system developed by Google, Inc. of Mountain View, Calif., fall within the intended definition of a mobile computing device. A great number of other mobile computing devices with similar or different operating systems, will also be applicable to the inventive subject matter, which is described at length below in connection with the description of the various figures. Mobile computing devices may include tablets or smart phones.

Figure 3:
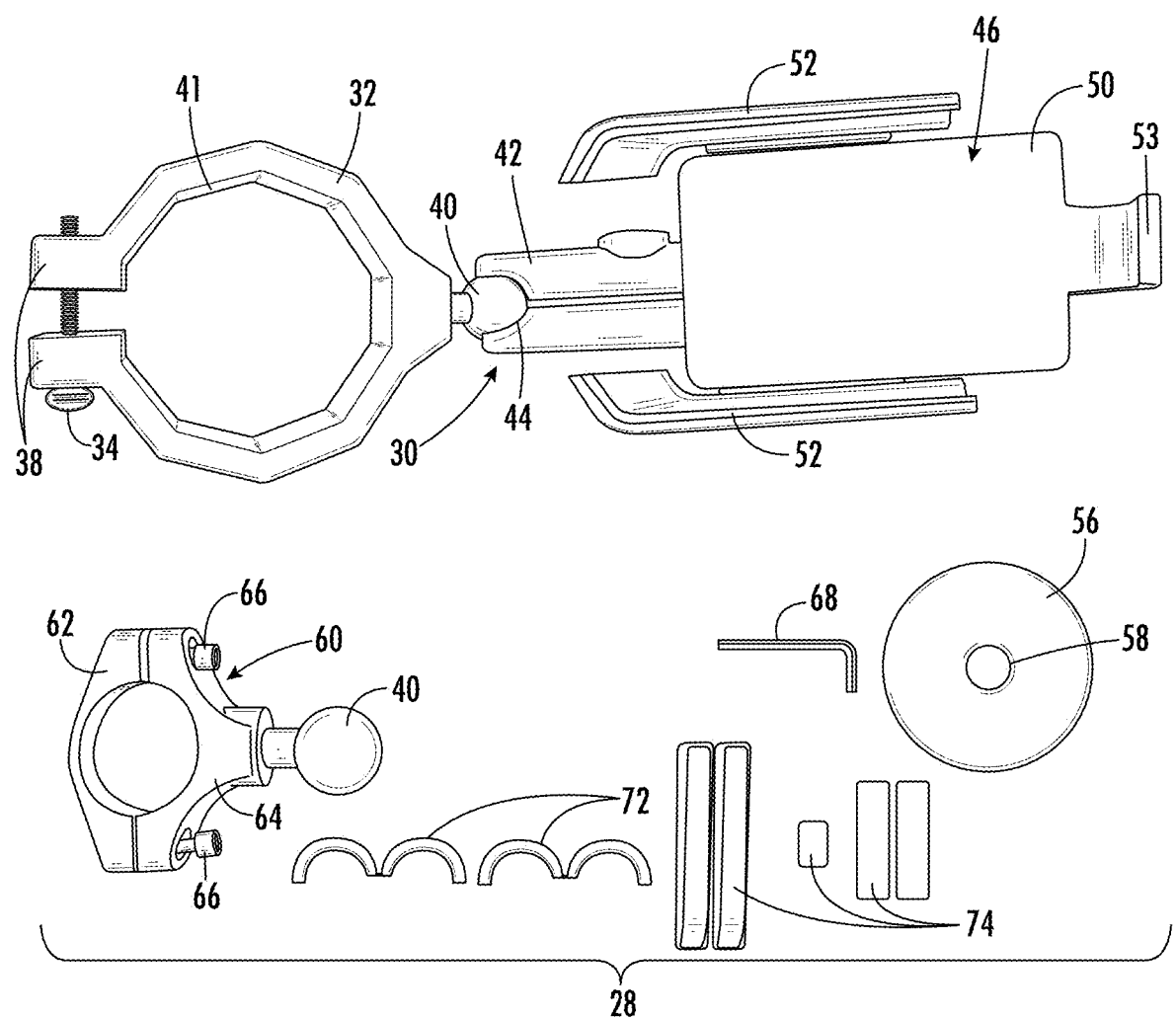
FIG. 3 is a top perspective view of a penetrometer adaption kit according to an aspect of the present disclosure.
Figure 4A:
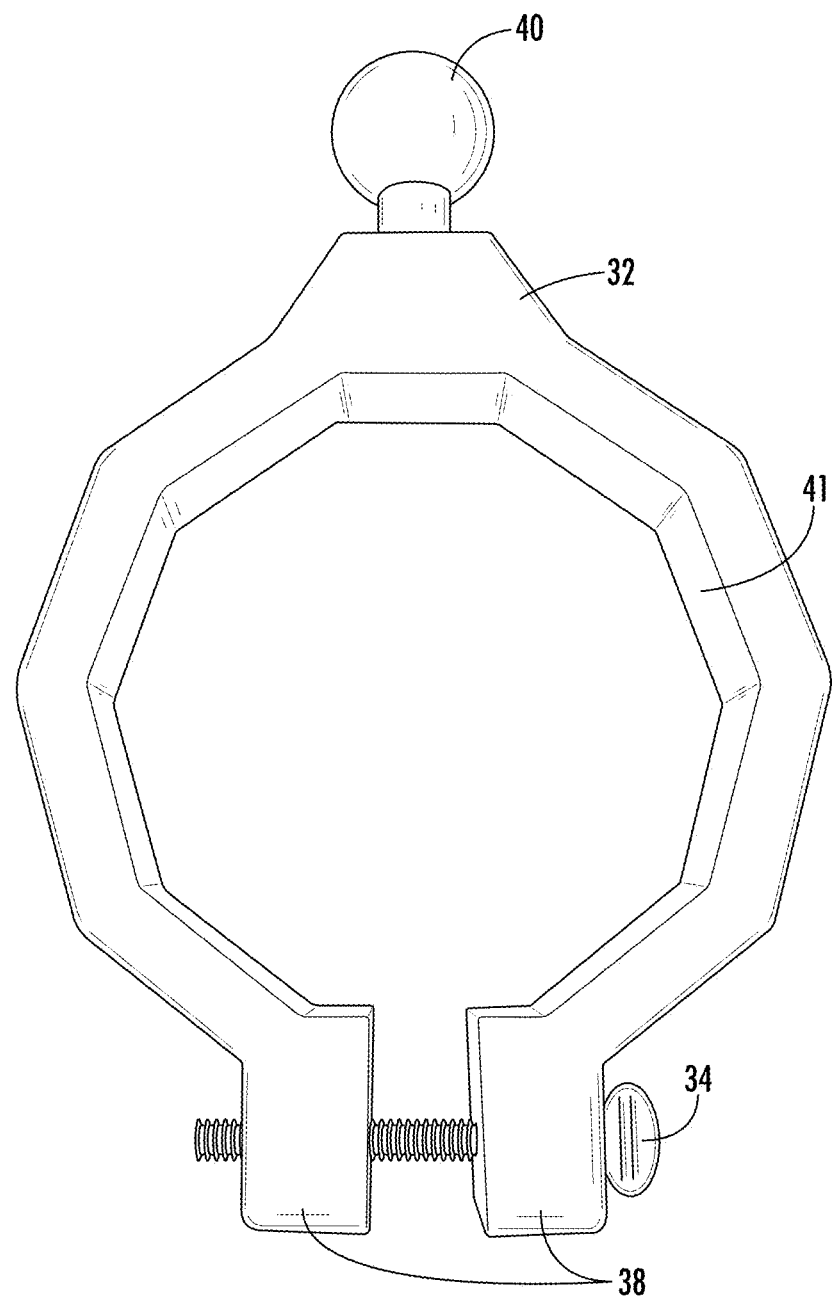
FIG. 4A is a top-down perspective view of a ring clamp with a hexagonal interior and exterior surface in order to properly attach to a hexagonal shaped surface of a penetrometer pressure gauge having a corresponding perimeter shape according to an aspect of the present disclosure.
Figure 4B:
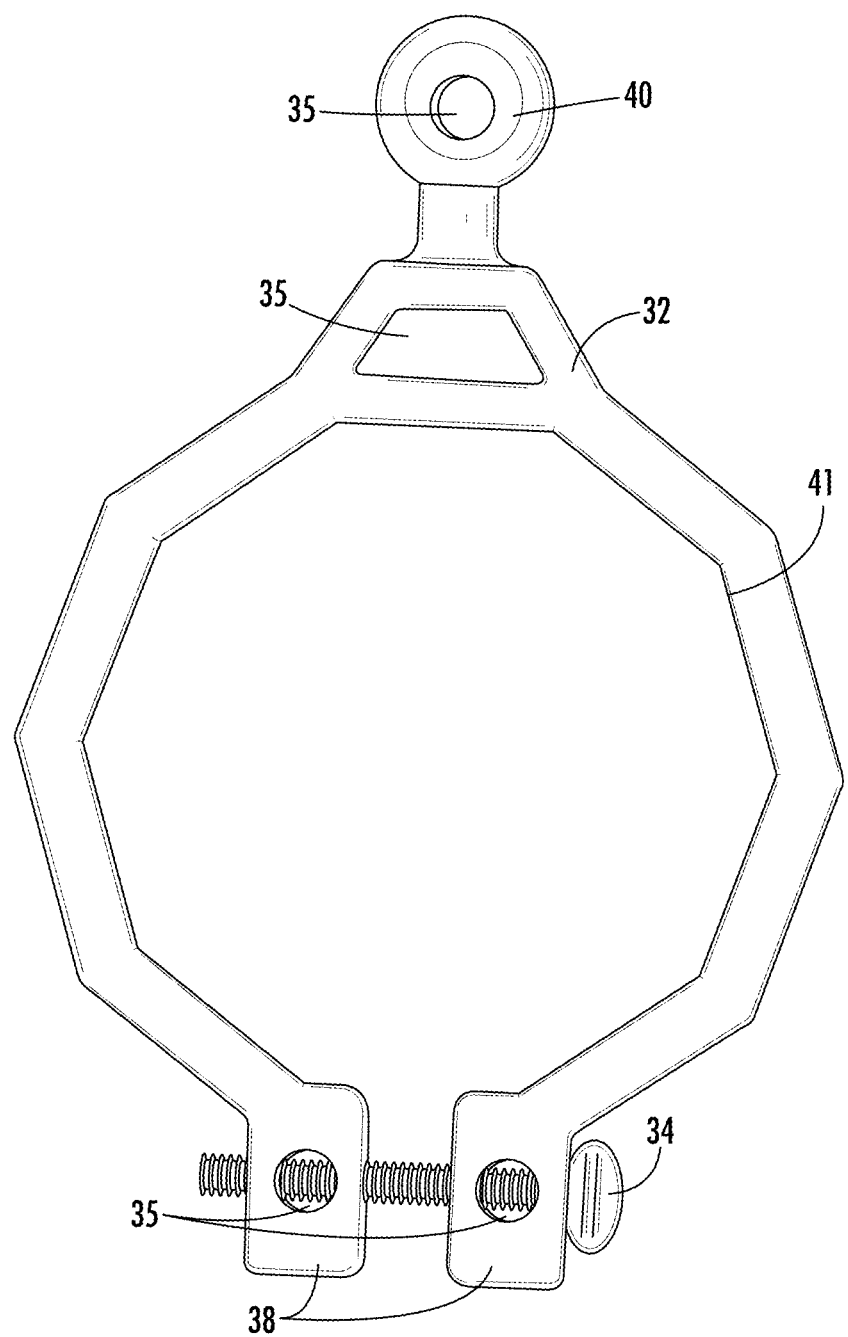
FIG. 4B is a bottom-up perspective view of the ring clamp of FIG. 4A and showing a number of bored out sections within the body of the ring clamp according to an aspect of the present disclosure.
Figure 5:
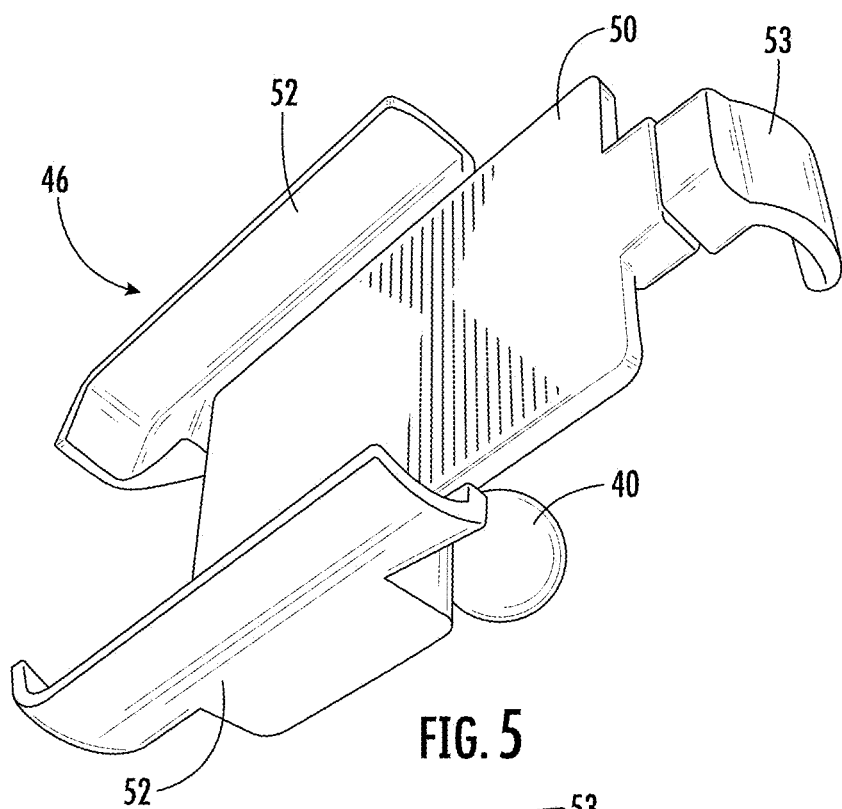
FIG. 5 is a side perspective view of the mobile computing device holder with the upper flange reversed to better and more easily receive a mobile computing device and oriented to not block either insertion of the mobile computing device into engagement with the holder or block a camera of the mobile computing device according to an aspect of the present disclosure.
Figure 6:
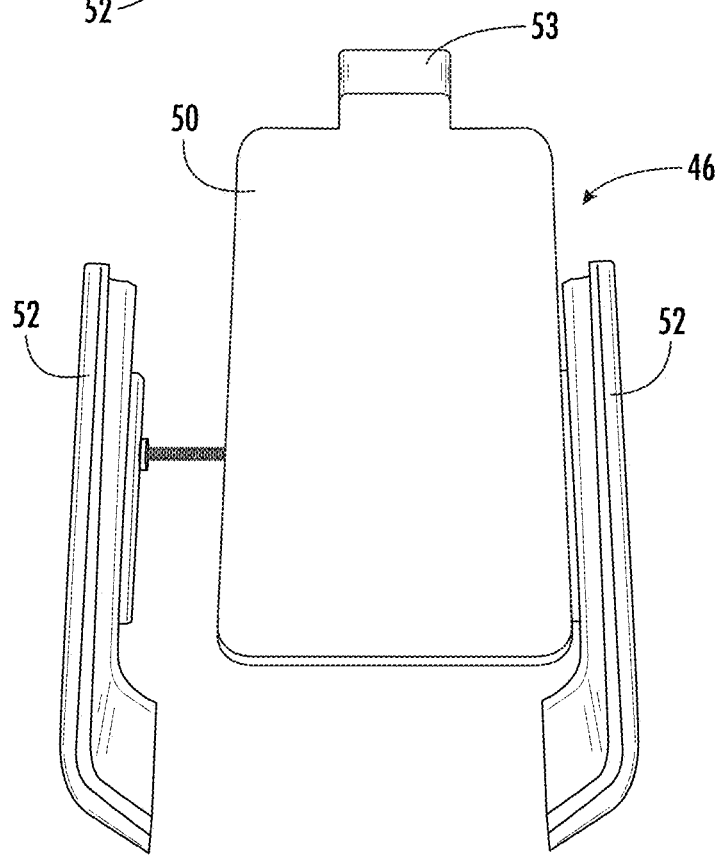
FIG. 6 is a top-down perspective view of a mobile computing device holder with a spring biased side flange extended outward according to an aspect of the present disclosure.
Figure 7:
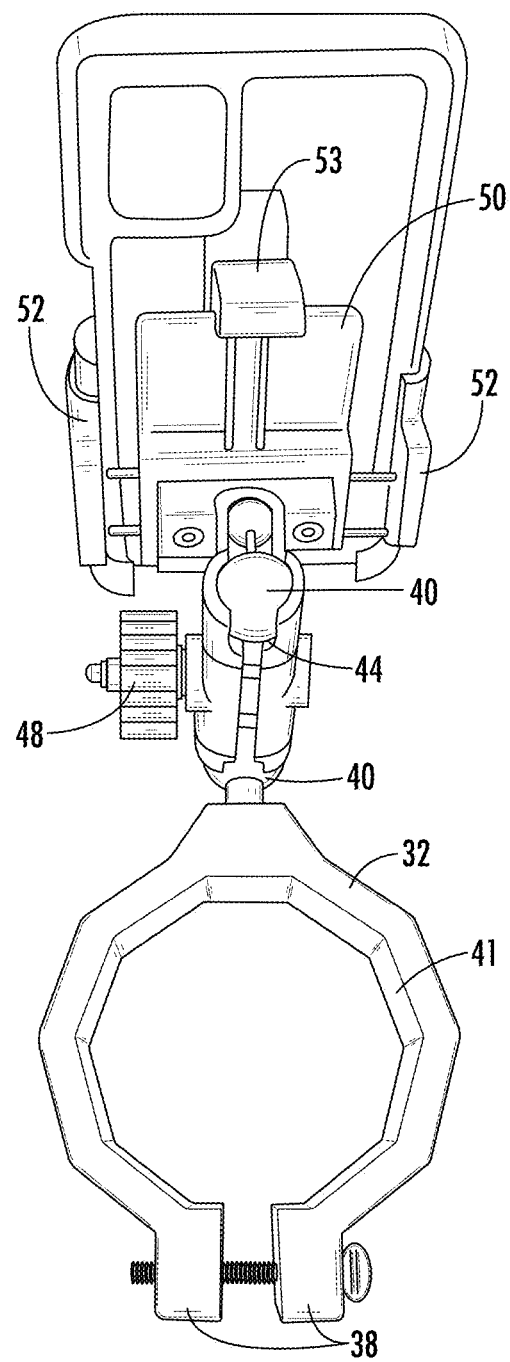
FIG. 7 is a rear perspective view of the mobile computing device attachment with a mobile computing device mounted in the mobile computing device holder according to an aspect of the present disclosure. The mobile computing device may be held in a vertical position, a horizontal position, or any other rotational direction about the ball joint.

As shown in FIGS. 3-9, the custom designed penetrometer and mobile computing device attachment system typically includes a ring clamp 32 to allow removable attachment of the system to an exterior perimeter surface of a pressure gauge 20 of the penetrometer 10 (FIG. 7). The mobile computing device attachment system also typically is designed such that a user may simultaneously view the screen of the mobile computing device and the display, if any, of the pressure gauge of the penetrometer. A mobile computing device attachment system of the present disclosure typically includes a ring clamp 32 that is typically substantially circular with two outwardly extending flanges 38 opposite a ball joint 40 on one side and defining an opening 41 defined by the interior surface of the ring clamp 32. As shown in FIGS. 4A and 4B, the ring clamp 32 may further include an embedded logo that is typically opposite the flanges 38 and adjacent the ball joint 40 on either both sides or the side that faces the user during use. As shown in FIG. 4B, ball joint 40 may have a bored hole 35 therein, which typically is not functional, but saves on material costs when injection molding the device. As shown in FIG. 3, the opening 41 of the ring clamp 32 is flanked on either side by pair of flanges 38 with a tightening hole. A thumb screw 34 passes through the tightening holes, and a threaded brass heat set insert is typically disposed in at least one of the ring clamp 32 tightening holes through which the thumb screw 34 passes. By turning the thumb screw 34, the flanges 38 will be either pushed together by the threaded brass heat set insert as it advances along the thumb screw 34 or they will be allowed to spread out as the threaded brass heat set insert retreats along the thumb screw 34 and the restoring force of the ring clamp 32 forces the flanges 38 into their original position further apart thereby allowing for the clamp to engage the pressure gauge 20 exterior perimeter on the penetrometer 10 in a releasable manner. In this way the ring clamp 32 can be easily attached and removed from the pressure gauge 20 by hand and without the use of tools. Alternative fastening devices may be used instead of thumb screws. For example, nuts and bolts, clevis pins, cotter pins, screws, and pins may all be used to secure the flanges together. The fasteners may also be permanent fasteners so that the ring clamp cannot be removed by hand.

The inside surface of the ring clamp 32 may have a knurling texture, or other texture, to retain engagement with the pressure gauge 20. The interior surface of the ring clamp 32 may have an elastomeric material thereon to facilitate engagement as well. Additionally, the outer surface of the ring clamp 32 may be differently shaped to correspond to the general shape of the exterior perimeter of the pressure gauge 20. Exemplary shapes are shown in FIG. 8, wherein the ring clamp 32 has a smooth circular shape or a hexagonal one. The ring clamps 32 may also include exterior padding along their outside surface and/or any other surface. The padding protects the rings clamps in case they are dropped or if they are hit or bumped in to when they are on a penetrometer. The padding partially absorbs the force of impacts and may be made out of rubber, plastic, leather, or any pliable, force absorbing material.

The mobile computing device attachment 30 further typically includes an adjustable midsection piece 42 with two ball sockets 44. The adjustable midsection piece 42 is attached to the ball joint 40 of the ring clamp 32 as well as a ball joint 40 of the mobile computing device holder 46. The adjustable midsection comprises two halves that can be brought together or distanced further apart. A tightener 48 can adjust the relative positions of the two halves. The two haves have shaped ends that form the ball sockets 44. The ball sockets 44 close around the ball joints 40, and tightening the tightener 48 will clamp the ball sockets 44 down on the ball joints 40. The mobile computing device/phone holder typically includes a rectangular base 50, and at least one upwardly extending side flange 52 and an upper upwardly extending flange 53 to hold a mobile computing device, typically a "smart" phone having a touch sensitive display in place. The at least one upwardly extending side flanges 52 are typically somewhat flexible, such that the user can bend the at least one upwardly extending side flange 52 with a small amount of force, but are resilient enough to retain their shape after insertion of the mobile computing device 26 into engagement with the holder. It is preferable that there are no flanges covering a portion of a mobile computing device where a charging cable or similar cable may be engaged. For a smart phone, the charging port is usually on the bottom side of the device, so the mobile computing device holder will not have a flange in that location.

In other embodiments of the disclosure, the mobile computing device attachment 30 uses one or more pivot joints instead of ball joints that allow for angular movement between different parts of the mobile computing device attachment 30. In other embodiments, a variety of different types of joints may be used simultaneously. Any number of joints may be used in order to allow the mobile computing device holder to be positioned however a user wishes. Alternatively, the movement may be restricted to only select angles or ranges. In some embodiments, the adjustable midsection may not be present, or there may be multiple adjustable midsections attached in series to change the movement profile of the adjustable mobile computing device attachment.

To attach a smart phone to the mobile computing device holder, the user presses it in towards the base, pushing the at least one upwardly extending side flange 52 until it fits around the perimeter of the smart phone. Typically, the user will position the upper upwardly extending flange 53 so that it is reversed as in FIG. 5 and extends downwardly in relation to the upwardly extending side flanges 52. Reversing the upper upwardly extending flange 53 allows the user to easily remove the phone from the phone holder since the pathway is unobstructed and also allows the smart device to take pictures without its camera becoming blocked by a flange 53. The at least one upwardly extending side flange 52 can be readjusted so that it is further away from the base and from another upwardly extending side flange 52. In this fashion, multiple sizes of smart devices can fit within the smart device holder. The upwardly extending side flange 52 can be seen in FIG. 6 in an extended position. Typically, the side flanges 52 are spring biased toward one another using a coil spring, a helical compression spring or other spring for supplying linear inward force.

Figure 19:
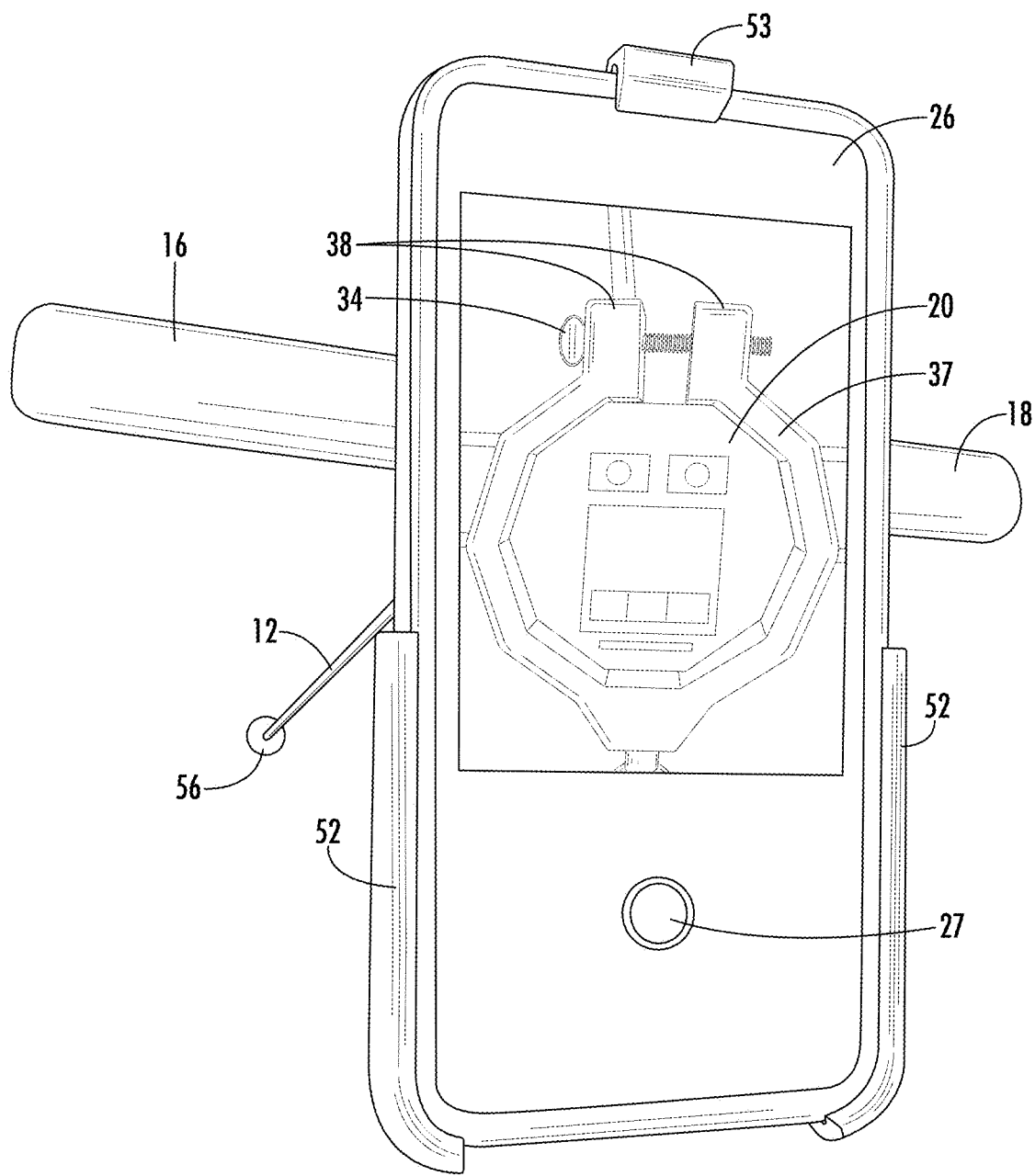
FIG. 19 is a view of a mobile computing device screen where the mobile computing device is using the camera of the mobile computing device and optionally the mobile application for taking measurements according to an aspect of the present disclosure to display the pressure gauge of the pentameter according to an aspect of the present disclosure. The camera function may be used to independently photograph the display of the penetrometer outside of the use of the mobile computing application of the present disclosure.

The mobile computing device attachment 30 can be repositioned in a variety of ways in order to conform with user preferences. Typically, the mobile computing device attachment 30 is positioned so the device is centered in a radial direction from the support rod 12 and not covering the pressure gauge 20 such that a user can see both the pressure gauge 20 and the phone screen when the user is grasping both handles and looking down from above both the pressure gauge 20 and the phone screen. In another possible arrangement, shown in FIG. 19, the mobile computing device 26 is positioned so that the pressure gauge 20 is visible from an onboard camera of the mobile computing device/smart phone 26, enabling a user to view pressure measurements on the smart phone screen while working in an application. The view of the pressure gauge may be seen in the mobile application while the user is inputting the pressure measurements. A live picture of the pressure gauge could be positioned proximate to the data entry fields in the data entry screen while it is in use. A user could toggle this feature on and off. The smart device may be equipped with enhanced photo detection software, allowing the smart device to collect penetrometer 10 data without input from a user. In this case, a penetrometer 10 should be inserted into the soil at a rate of around one inch per second, to ensure that the smart device camera can accurately record the measurement displayed on the pressure gauge 20, typically via video or via visual character recognition as discussed in more detail herein. The constant rate insertion may be assisted by a timer shown on the screen of the mobile computing device so that a user can more easily time their movements. The users could alternatively, click the photo button 27 on the screen to take a picture or screenshot of the penetrometer display through the smartphone camera at every notched interval on the rod of the penetrometer. This would substantially reduce the amount of manual data entry for the user. These photos could then be processed through a camera vision system and an image recognition software would identify and log the measurement at each depth.

In a potential embodiment, the mobile computing device attachment 30 is integrally attached to the penetrometer 10, and cannot be removed by hand. This embodiment would use an integral ring clamp, or no ring clamp at all, with the adjustable midsection or the mobile computing device holder being attached to the penetrometer directly. The connection may be anywhere along the support pole or on either of the handles. Preferably, the connection is near the gauge so that the user may easily view both the gauge and the mobile computing device simultaneously. The connection may still be adjustable, so that the mobile computing device may be moved, or the connection may be stationary and the mobile computing device is in a set location.

In a potential embodiment, the mobile computing device attachment 30 could be a bolt or rod that extends horizontally from the penetrometer 10 at a 90° angle from the support rod 12 and is located at the intersection of the support rod 12 and the handles as discussed herein. The mobile computing device attachment 30 may possibly be in the form of a bolt that can screw into a hole located at the intersection and is long enough to allow for a removable connection with the mobile computing device holder 46. The mobile computing device 26 and its related attachment mechanism could be attached to other areas of the penetrometer 10 as opposed to the pressure gauge 20. Depending on the model of the penetrometer, the pressure gauge may not be positioned above the handles of the penetrometer and attachment of the mobile computing device attachment to the gauge may not be convenient or may affect the balance of the penetrometer. In this case, the mobile computing device may instead be attached elsewhere, such as to the support rod 12 or either of the handles.

A smartphone enhanced soil penetrometer kit 28 typically includes a leveling plate 56 that is placed along the support rod 12 and can slide up and down the rod surface. The leveling plate 56 is large enough that the support rod 12 passes through the leveling plate hole 58 located centrally in the leveling plate 56 and wherein the leveling plate hole 58 is large enough to accommodate the diameter of the support rod 12 but still small enough that the leveling plate 56 will catch on a cone 24 that is attached to a bottom end of the support rod 12 and will not slide off without user intervention. The size of the leveling plate may vary depending on the soil condition. For soils that are relatively flat, the leveling plate may be smaller. For more uneven soils, a larger leveling plate will better approximate the actual soil surface. To assist with usage of the leveling plate 56, the notches 22 may be made to be wider, so that they are more visible against the rest of the support rod 12. Alternatively, the notches 22 may be colored or the support rod 12 may be colored around the notches 22. The colors may be painted on, or applied by similar means. The notches 22 may also have numbers located next to them indicating their depth in inches or an alternative measurement. The numbers are upside down in order to be viewed from above by a user of the penetrometer who is looking downwards towards the ground. The number may be painted on, or may be represented by stickers having a number printed on them or having a number shape. They are also visible from any side of the support rod 12, typically by being printed multiple times around the exterior of the support rod 12. The leveling plate 56 may also come with a variety of colors/patterns in order to visually differentiate it from the notches 22 or the rest of the support rod 12. Conceivably there may be an illumination source within the penetrometer 10 that causes light to be transmitted out the "notches 22" to illuminate the locations for measurement. The illumination source may be one or more light emitting diodes and the locations for the "notches 22" constructed of a transparent material allowing transmission of light such as a plastic. Illumination may also be provided by a flashlight feature on the mobile computing device. The entire penetrometer 10 could conceivably be made of a material other than plastic, provided it had the strength and other features necessary to perform the soil compaction measurements. The penetrometer may be made out of metal, such as aluminum or steel. Also, the notches 22 might be replaced with a circumferential rim protraction with one or more notches 22 that allow the leveling plate 56 to pass over them into different heights/locations. This would not typically be desired due to the potential difficulty in movement of the leveling plate 56 to all the different heights needed, but could be employed nonetheless as one or more of the locations for measurements.

Crop production land is never perfectly level due to past tillage and leftover crop residue from previous years of crops. The mild deformities in the soil surface make finding the exact surface harder, and a user may place the penetrometer 10 at the incorrect depth because they were measuring in relation to their perceived surface level as opposed to the real surface level or the average surface level. Readings that are taken even a few inches off from the correct surface level can skew the data collected by the penetrometer 10 and significantly impact how a user's conclusions on how to till the field being tested. The leveling plate 56 placed along the support rod 12 helps show where the true surface of the soil is as the force of gravity will pull the leveling plate 56 as far as it can slide down the support rod until it hits an obstacle/the ground that can oppose it. The leveling plate 56 will come to rest on the true surface, which helps the user visualize it and thereby make more accurate readings relative to the surface and ensures their data will be a more realistic representation of their field's soil density. In addition, the leveling plate 56 can also keep the support rod 12 clean off dirt and other debris. The leveling plate 56 will slide down the support rod 12 when it is removed from the soil after testing and wipes off the debris. As the user may use notches 22 on the support rod 12 to read the depth, keeping these notches 22 clear of dirt will greatly assist the user in seeing where exactly the notches 22 are and whether it lines up with the leveling plate 56 or not. The hole of the leveling plate may have a seal. The seal helps the leveling plate stay in frictional contact with, and better clean, the support rod 12. The hole may instead include prongs or tines that scrub the support pole 12.

In a potential embodiment, the leveling plate may include a sensor to detect the notches on the support pole. The sensor allows the penetrometer to alert the user when the leveling plate has reached the correct notch, and thus, depth, without the user needing to visually identify it themselves. The sensor may be an optical sensor that detects the visual difference of the notches from the surrounding material of the support pole. When a notch is detected, an alarm may sound or a visual pop up may be displayed on the screen of the mobile computing device so that the user knows to pause inserting the penetrometer.

Instead of using solely a leveling plate 56 and notches 22 to determine the depth of the penetrometer 10 support pole in the soil, lidar sensors may be used instead of, or in addition to, the notches 22. Light detection and ranging (LIDAR) sensors are sometimes included on mobile computing devices or other handheld devices or could conceivably be included with the penetrometer itself. When the mobile computing device 26 or other device having one or more LIDAR sensor are held perpendicular to the ground while the penetrometer 10 is inserted into the soil, the LIDAR sensor measures the distance to the soil surface. The depth of the penetrometer 10 can then be calculated from the distance from the ground while inserted and the usual height of the phone above the ground when not in use. When a depth intended to be measured by the penetrometer is reached, the mobile computing device 26 may alert the user. The alert may be in the form of a pop up on the screen or possibly an audio cue. Because the lidar sensors can be very accurate, the leveling plate can be relatively small. In other penetrometer systems with a plate, the plate is very large and cumbersome, and may be around a foot long. The leveling plate of the present disclosure makes the penetrometer easier to move and will not hamper a user's movement. LIDAR sensors are also easier to use with a smaller leveling plate. A large leveling plate may block the LIDAR sensors from reaching the actual soil surface, and prevent it from getting an accurate soil depth reading. When larger leveling plates used in connection with penetrometers are employed, the larger leveling plates are also not fixed to the penetrometer, meaning the user must pick up and carry both the penetrometer and leveling plate separately between each measurement location. When LIDAR sensors are used in the systems of the present disclosure, the leveling plates of the system may be significantly smaller. The leveling plates in such instances typically would be symmetrically shaped across a line passing thought the support rod and typically would not have surface area greater than four square inches.

Ultrasonic sensors, which generally use the larger leveling plates, may also be used to measure the soil depth. However, it is preferable to use LIDAR sensors in the context of the present disclosure because they are generally more accurate than ultrasonic sensors. In another alternative embodiment, the penetrometer system may instead use GPS to determine its elevation or height above sea level in order to find the depth. As the penetrometer is pushed into the soil, the elevation will change. By comparing a new measured elevation to a previous measured elevation, the depth of the penetrometer 10 can be determined automatically by the software application or the mobile computing device. Tracking the penetrometer's elevation will require a sufficiently strong and accurate GPS system.

Another aspect of the penetrometer kit 28 is the monitor bar adapter 60. The monitor bar adapter 60 includes a bar clamp to attach to a monitor bar, or similar attachment accepting structure, in a vehicle, such as, a tractor or combine. The monitor bar is typically a horizontally positioned bar in the interior of a tractor cabin or other farm vehicle cabin. The bar clamp has two non-unitary pieces, a securing side 62 and joint side 64 that are connected to one another through at least one bar clamp tightener 66 passing through the securing side 62 and the joint side 64 via a receiving hole. The bar clamp thumb screw 34 can be tightened by means of a hex key 68. Both the securing side 62 and the joint side 64 have a bar interfacing surface shaped to conform with a standard monitor bar. To attach the monitor bar adaptor, a user starts by placing each side of the monitor bar adaptor on opposite sides of a bar while they are separated into two pieces, while lining up the receiving holes with at least one bar clamp thumb screw 34. Once the one bar clamp tightener 66 is partially inserted into a receiving hole, the hex key 68 is used to turn the one bar clamp tightener 66 and tighten the bar clamp. The joint side 64 also typically includes an adapter ball joint 70 that interfaces with the adjustable midsection piece 42 and phone holder of the phone attachment. In this way a user can use the phone attachment on a penetrometer 10 or in a vehicle and modify the phone attachment to do so without the use of tools. The monitor bar adapter 60 also includes one or more spacers 72. When joined together, the securing side 62 and the joint side 64 form a circular space through which the monitor bar passes through. The monitor bar may not perfectly fit, so the spacers 72 fit inside the space and around the monitor bar to make up the space. The monitor bar adapter 60 may also include adhesive strips 74 to better lock the smart device in the smart device holder.

In some aspects of the present disclosure, the penetrometer may include an integrated computing system and the penetrometer system may not use, or only partially use, a separate mobile computing device. The penetrometer may include an integrated display, which displays the software application and may give the user access to other features of the integrated computing system. The display may be touch sensitive and allows the user to control the application and record data by physically touching the display. The penetrometer may not have a gauge separate from the display, and may instead show the pressure readings of the penetrometer alongside the software application on the display. Readings from other sensors on the penetrometer are also sent to the display. The estimated depth, moisture readings, temperature, and GPS coordinates can all be shown on the display simultaneously, or upon selection by a user. To record pressure measurements, the user first inserts the penetrometer into the soil to the desired depth. When the depth is reached, the penetrometer may have a pop up or other visual and/or auditory alert shown on the display or played by an onboard speaker. The current detected pressure can then be recorded by the user by pressing a button or display. In some embodiments, the recording may be done automatically when the penetrometer senses that it is at the predetermined depth where a measurement is prescribed. The penetrometer may have an internet or WIFI® connection to link the penetrometer to an external server. The software application, the survey data, or both may be located on the external server, or in computer memory onboard the penetrometer's integrated computing system.

The penetrometer 10 may have an onboard power system. Typically, the power system is one or more rechargeable or replaceable batteries. The penetrometer system may have solar panels to collect energy that may supplement the batteries or serve as the sole power supply for the penetrometer. Solar panels constantly replenish the energy used by the penetrometer integrated computing system or digital pressure gauge. If the penetrometer uses an external mobile computing device to record data, a charging cable may be connected the penetrometer to the mobile computing device so that the mobile computing device can recharge using the penetrometer's power supply. A charging cable may include with the penetrometer in a penetrometer kit, or it may be integrated with the penetrometer and can be extended from the penetrometer's casing. The battery life of the power supply typically lasts 12 to 24 hours. Because fields may vary in size and the farming organization may want to collect different numbers of data samples, the battery life should be long enough to power the penetrometer throughout the entire average data collection time period for at least a single field. An average field of 40 acres may take a user an hour to complete, but a user may have more fields to perform measurements in. A user could theoretically complete 380 acres worth of fields in a single day.

Most of the systems of the mobile computing device or the penetrometer will be connected using a cellular or WIFI® connection, for example. Exemplary computing systems used in connection with the methods and systems of the present invention can include one or more of the implementations of the technology described herein. A computing system can include one or more panel processors and peripherals, and a panel subsystem associated with an input device (which may correspond to a mobile computing input device). Peripherals can include, but are not limited to, random access memory (RAM) or other types of memory or storage, watchdog timers, and the like. The panel subsystem can include, but is not limited to, one or more sense channels, channel scan logic and driver logic. The channel scan logic can access Random access memory, autonomously read data from the sense channels and provide control for the sense channels. In addition, channel scan logic can control driver logic to generate stimulation signals at various frequencies and phases that can be selectively applied to drive lines of a touch sensor panel. In some implementations, the panel subsystem, panel processor and peripherals can be integrated into one application specific Integrated circuit (ASIC).

A touch sensor panel can include a capacitive sensing medium having a plurality of drive lines and a plurality of sense lines, although other sensing media also can be used. Each intersection of drive and sense lines can represent a capacitive sensing node and can be viewed as a picture element (pixel), which can be particularly useful when the touch sensor panel is viewed as capturing an "image" of touch. In other words, after the panel subsystem has determined whether a touch event has been detected at each touch sensor in the touch sensor panel, the pattern of touch sensors in the multi-touch panel at which a touch event occurred can be viewed as an "image" of touch (e.g., a pattern of fingers touching the panel). Each sense line of the touch sensor panel can drive the sense channel in the panel subsystem. The touch sensor panel can enable multi-touch gesture detection so that shapes can be generated and modified according to implementations of the technology.

The computing system of the mobile computing device or penetrometer also can include a host processor for receiving outputs from the penetrometor processor and performing actions based on the outputs that can include, but are not limited to, moving an object such as a cursor or pointer, scrolling or panning, adjusting control settings, opening a file or document, viewing a menu, making a selection, executing instructions, operating a peripheral device coupled to the host device, answering a telephone call, placing a telephone call, terminating a telephone call, changing the volume or audio settings, storing information related to telephone communications, such as addresses, frequently dialed numbers, received calls, missed calls, logging onto a computer or a computer network, permitting authorized individuals access to restricted areas of the computer or computer network, loading a user profile associated with a user's preferred arrangement of the computer desktop, permitting access to web content, launching a particular program, encrypting or decoding a message, prompting the generation of a signal of any kind, and/or the like. The host processor also can perform additional functions that may not be related to the use of the penetrometer, and can be coupled to a program storage medium and a display device (which may correspond to the computing system) such as an LCD display for providing a user interface to a user of the device. The display device together with the touch sensor panel, when located partially or entirely under the touch sensor panel, can form a touchscreen.

One or more of the functions described throughout the above application can be performed by instructions (e.g., programming, software, firmware) stored in memory (e.g., one of the peripherals) and executed by the processor of the mobile computing device, or stored in the program storage and executed by the host processor. The instructions also can be stored and/or transported within any computer-readable storage medium for use by or in connection with an instruction execution system, apparatus, or device (hereinafter referred to as "instruction execution system"), such as a computer-based system, processor-containing system, or other system that can fetch the instructions from the memory. In the context of this document, a "computer-readable storage medium" can be any medium that can contain or store the program of instructions for use by or in connection with the instruction execution system. The computer readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such as CD, CD-R, CD-RW, DVD, DVD-R, or DVE-RW, or flash memory such as compact flash cards, secured digital cards, USB memory devices, memory sticks, and the like.

In some embodiments, the mobile computing device has a graphical user interface (GUI), one or more processors, memory and one or more modules, programs or sets of instructions stored in the memory for performing multiple functions. In some embodiments, the user interacts with the GUI primarily through finger contacts and gestures on the touch screen display. Executable instructions for performing the functions of the presently described methods and systems may be included in a computer readable storage medium or other computer program product configured for execution by one or more processors of the mobile computing device.

Building on the discussion above, in other words, aspects of the methods and systems of the present disclosure may be achieved, at least in part, by software stored on a non-transitory tangible computer readable medium or software modifications or updates to existing software residing in a non-transitory computer readable medium. Such software or software updates may be downloaded into a first non-transitory readable media of a controller (or locally associated with a controller or some other processor) typically prior to being installed in a mobile computing device or the penetrometer from a second non-transitory computer readable media located remote from the first non-transitory computer readable media, i.e., a server system.

Figure 9:
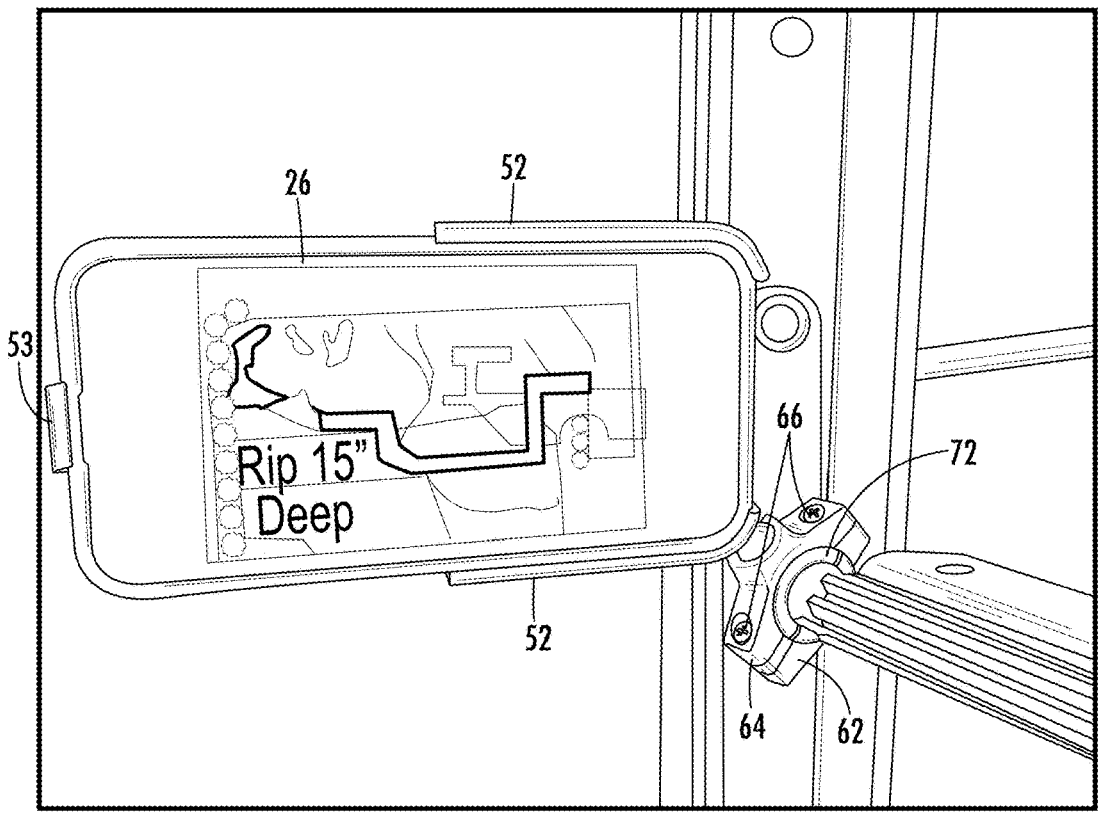
FIG. 9 is a view of a satellite map with data entry points created by the software application and penetrometer system in landscape mode while utilized in conjunction with the monitor bar adapter according to an aspect of the present disclosure.

To easily understand their field's compaction levels, a user can use a software application on the mobile computing device that displays satellite images of their fields along with a number of data points corresponding to areas in the field where penetrometer readings were taken (FIGS. 10A-17B). A series of individual data points with associated GPS coordinates can be difficult for a user to interpret, and as a result it will be hard to discern how to best change their tillage tactics. A major obstacle for a user is that they may not always have an accurate idea of what section of their field or fields corresponds with the GPS coordinates of the individual data points. Creating an overall tillage recommendation map (FIG. 18) that includes tillage recommendations for segments of the overall tillage recommendation map, where the segments are displayed based on the soil profile at different locations and the different tillage recommendations for the segment, can alleviate the problem by giving users a visual representation of where in their fields a particular kind of tillage must be employed. FIG. 9 shows the tillage recommendation map on the smartphone within a user's vehicle. A user views this map while driving the vehicle, which may be a tractor or other farming vehicle equipped with a tillage implement or possibly a cover crop seeder. The current location of the user in the vehicle is shown on the map, so that the user can see in real time what section of a field they are in from above and compare their location to where different tillage recommendations are. When the user passes to a region on the map with a new tillage recommendation, they can change out the settings from the tillage in real time while never needing to leave the field. If a tillage recommendation requires the use of a different implement, then the user can leave the field, replace the tiller/cultivator, and return to the marked region on the map and continue on. For example, a user may need to begin with a chisel plow, but switch to a disk plow in the same section of field later or in other parts of the field.

Figure 14:
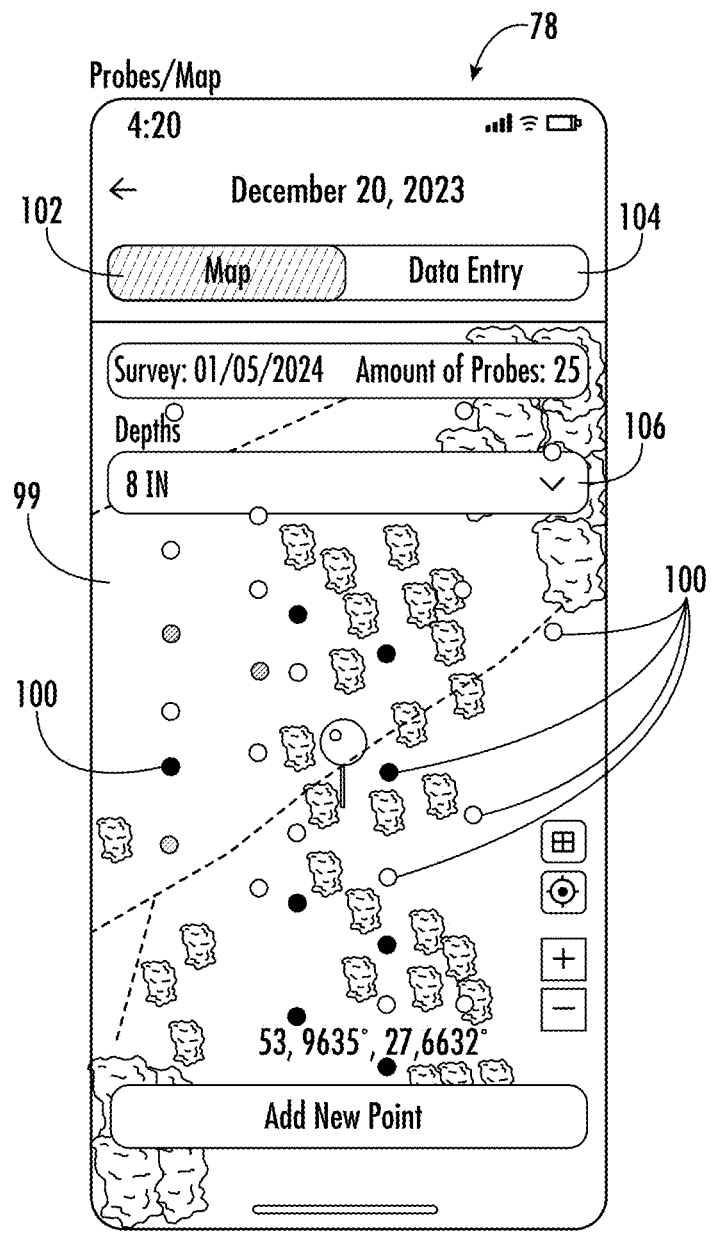
FIG. 14 is a graphical user interface of a map screen having a graphical topographical map to display on the mobile computing device during use to record and evaluate readings at different geographical locations at different depths of the soil to determine and evaluate the level of compaction of the soil at a plurality of locations that are graphically displayed according to an aspect of the present disclosure.

The application uses geographical information systems (GIS) software, such as the GOOGLE EARTH API®, to map data points to their corresponding locations on a satellite map. Alternatively, the application itself may be an API that may be added to other software. FIG. 14 shows how data points on a map will appear on the display of the application. Satellite maps can also help to show the user the topography of the field at all data points. If a group of data points are displaying a similar soil density profile, it could be explained as a result of a topographical feature of the area the group is in. For example, if the area is lower than the rest of the field, it could be prone to higher average saturation levels which would lead to an increased risk of creating compaction and thus lead to a large difference in compaction from its surrounding areas. Overly wet areas lead to increasing levels of compaction. Groupings of similar data points may also be explained by consistent use of farming vehicles in those areas. Farmers may use controlled traffic farming to limit repeated traffic passes to specific areas, thus minimizing the amount of a fields surface area that could be damaged by compaction. As long as the farmer knows the entrances/exits of the field, the regions of traffic cause compaction may be calculated and used by a controlled traffic system to plan routes through the field that minimize vehicle compaction.

It may be possible to take data from the systems of the present disclosure and geolocation information to automatically change the nature of the tillage being undertaken at a given location on a field during tilling such that when the user traverses over one segment of the overall tillage recommendation map into another based on the readings from the penetrometer the tillage settings on a piece of farm equipment may automatically adjust to make the appropriate tillage occur. This may be done through a real-time interface with the farming equipment or through the use of the application within the farming equipment itself and not on the mobile computing device or through transfer of the data from the mobile computing device to the farming equipment and/or tractor, for example, and the data used in real-time thereafter.

To access the software application, a user must have an account or create one if they currently do not. When a user enters the application for the first time, they will be prompted to make and account or log in to an existing account. Once, logged in, the application may remember that the user is logged in and the device that they are logged in with. This way, a user may not need to repeatedly log in when they access the application with a particular device. A single account may be linked with one or more mobile computing devices, and it may be able to be accessed simultaneously from multiple mobile computing devices. Each account has data stored therein. In particular, the application will have identifying data stored that helps the application verify a user's identity as well as aid them in account recovery if the account's log in credentials were lost. Information relating to farming organizations that the user has access to will also be stored. A user may only belong to a single farming organization, or they may be associated with several. Farming organizations themselves may restrict access to their data to select users as dictated by organization associations stored in their account. Affiliation with a farming organization may give user's access to particular crop fields managed by the farming organization as well as surveys done at those fields. Additionally, the account may have data for one or more penetrometers used by the user stored therein. The data for the penetrometers includes the brand or model of the penetrometer, as well has the physical characteristics of the penetrometer such as the number of notches. A user may change the settings related to the penetrometers by interacting with a link within their profile that leads to a probe configuration screen.

The application may instead be a browser-based application that a user accesses using an internet search browser. A user does not need to download an application onto a mobile computing device, and instead only needs an account and an internet or WIFI® connection to access the application web site. The supplication may also be located on a private server, such as a corporation's server or farming organization's server and accessible through an employee portal or similar system. A farming organization may subscribe to their own custom version of the application that is only able to be used by their own employees and that is kept separate from publicly available versions accessible through a web browser or downloadable application. Survey data relating to a farming organization's fields may be stored on their own server as well. Some versions of the software application, such as a custom version designed for a farming organization, may provide the estimated yield loss.

Users may also reset the password from their profile. Alternatively, a user may reset it by sending an email link in the case where they have forgotten or misplaced the password. A user may also reset the email address linked to the account. A user may optionally sign up for a subscription through the application. The user may be billed through the application or elsewhere. One or more features may be absent or limited for a user without a subscription. The application may provide a free trial, wherein a user may enjoy all features of the application during a limited period of time.

Within the software application, a user is able to navigate to different sections of the application by interacting with a link that appears as a visual icon on the screen of the mobile computing device of the user. The links may bring the user to a new screen, such as a user pressing a data point displayed on a map to bring up a data entry screen with the data listed for the data point that was selected. Alternatively, the selection of a link may create a pop up or menu that covers a portion of the screen of the mobile computing device. Pop ups and menus may have additional links or data fields that can be filled with data.

Figures 10A, 10B:
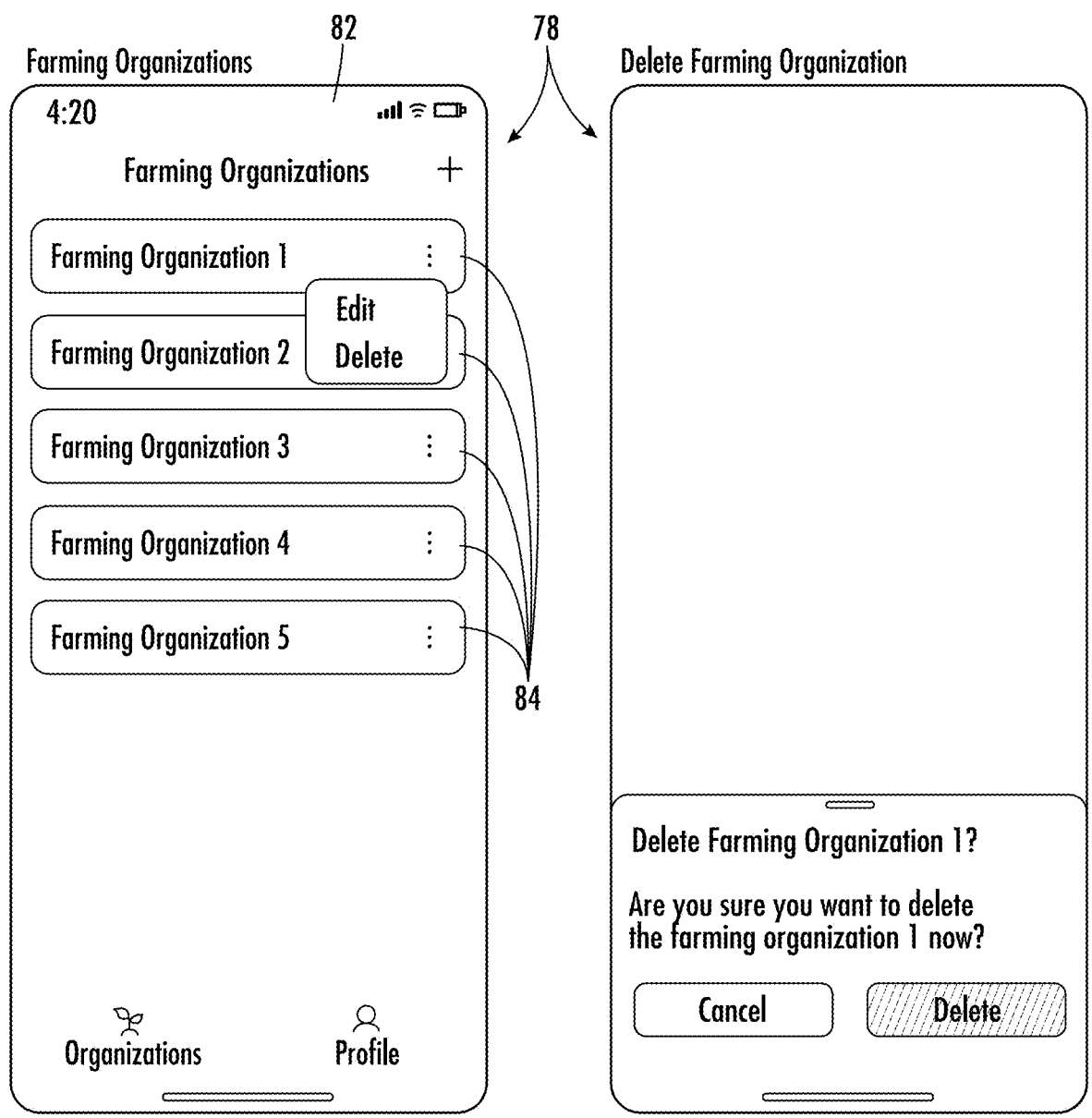
FIG. 10A is view of a graphical user interface of a mobile computing device's software application showing an exemplary farming organization selection screen according to an aspect of the present disclosure.
FIG. 10B is a view of a graphical user interface of a mobile computing device's software application showing a deletion confirmation pop up that appears at the bottom of the farming organization selection screen as in FIG. 10A when the user attempts to delete an instance of a farming organization according to an aspect of the present disclosure.
Figure 13A:
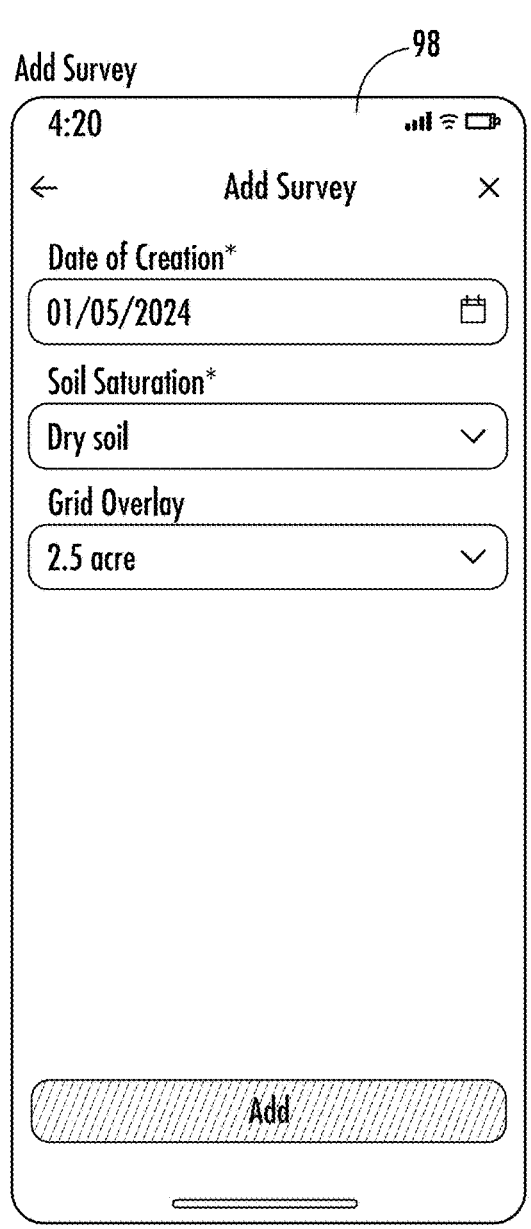
FIG. 13A is a graphical user interface of an add survey screen of a mobile computing application according to an aspect of the present disclosure.
Figure 13B:
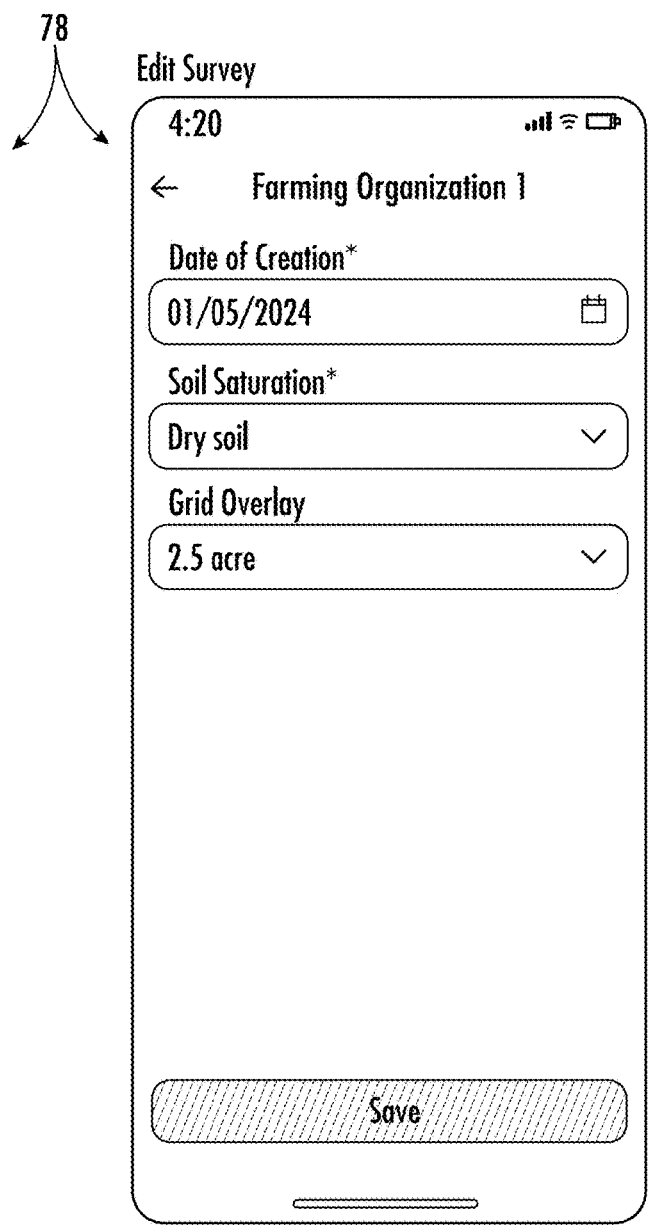
FIG. 13B is a graphical user interface of an edit survey screen, which is very similar to the add survey screen of FIG. 13A but with a listing of the organization and a save button as opposed to an edit button according to an aspect of the present disclosure.

When opening the app for the first time, or any time thereafter, the user may be presented with the welcome screen. The welcome screen may be shown while the application loads. Following opening the application, the user will be presented with an organization screen 82 as shown in FIGS. 10A-10B. The organization screen shows each farming organization that the user has saved data for, and which may be dictated by their account information or permissions from a farming organization. In the context of the present disclosure, a farming organization may be any individual farm or collective of farms or a company that owns multiple farming locations. The organizations may be business entities, individuals or groups of individuals or one or more farms, for example. Each organization 84 is displayed as a link that the user may interact with. The organizations may be the user's own farm or farms and/or a corporation or other organization.

Organizations may be added or deleted from the organization screen. If the application has been accessed for the first time, and the user has just created their account, there may be not be any organizations present. The user may be immediately prompted by the application to add an organization if there are none. From the organization screen 82, the user may select an organization 84 in order to direct them to a field selection screen 90. The field selection screen, as in FIG. 11, displays each field 92 belonging to the selected organization as a interactable link presented on the display of the user's mobile computing device. The fields 92 may have had surveys performed for them. If the user enters the fields selection screen 90 and there are no fields to display, they will need to add one. A user may add or delete fields within the field selection screen. The fields may be limited by permissions given by the farming organization or the user's account settings. The user may be able to view fields saved that were added by another user. This allows multiple users associated with an organization to work simultaneously in recording data for a given field. The user may select a field 82 in order to display a survey screen 94 as in FIG. 12. The survey screen shows each survey conducted previously at the selected field and gives the user the ability to create new ones. The user may add a survey or delete an existing one in the survey screen 94. The surveys may be surveys that were created by the user, or they may have been conducted by a separate user associated with the same organization so that multiple users can monitor a particular field. A user can view past surveys by interacting with one of the surveys listed.

Figure 15A:
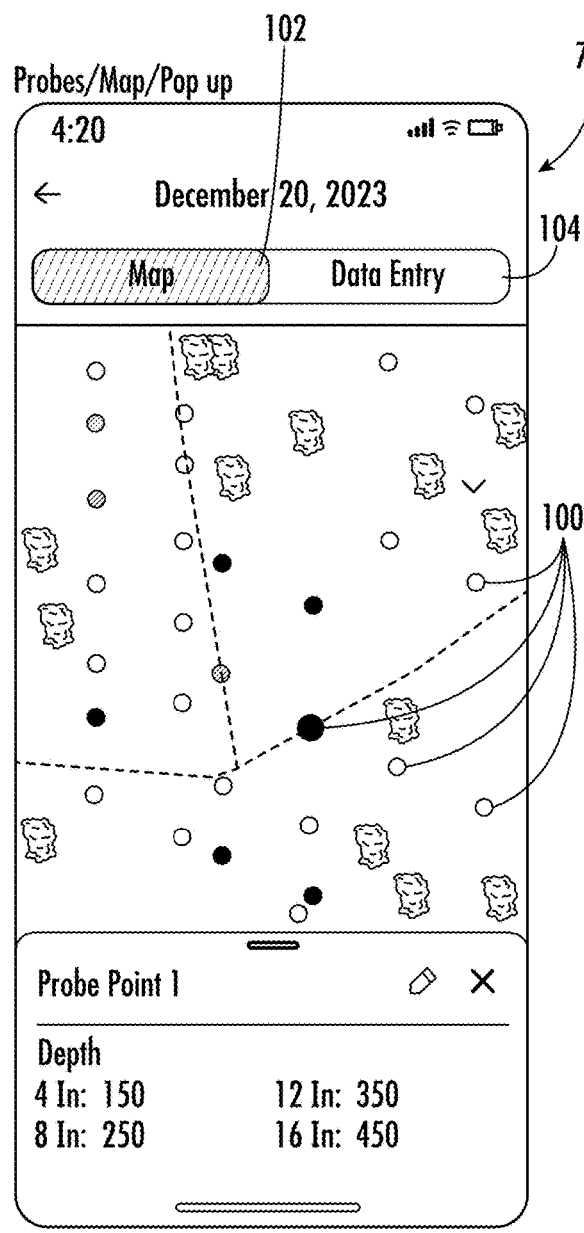
FIG. 15A is a graphical user interface of the map screen shown in FIG. 14 but with a data entry point on the graphical topographical map indicating an area where compaction level data was taken selected according to an aspect of the present disclosure. A probe point selection pop up is present at the bottom of the graphical user interface that a user may use to view and edit previous entries.
Figure 15B:
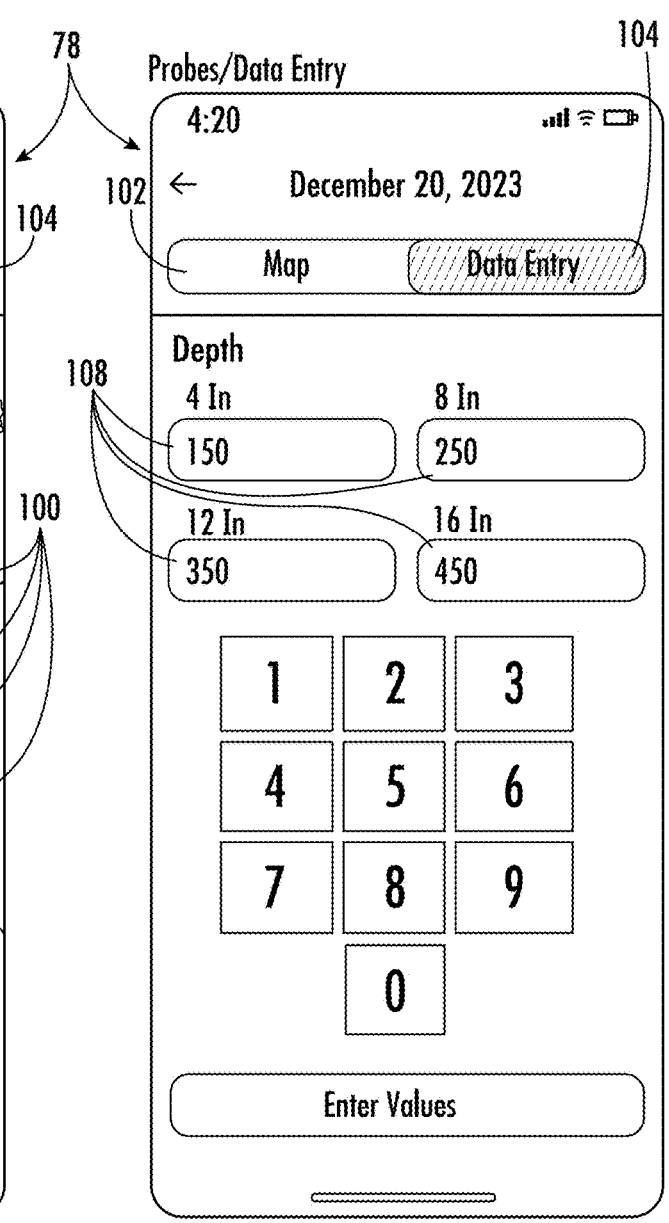
FIG. 15B is a graphical user interface of a data point entry screen wherein a user can input readings taken with the penetrometer and input them into fillable fields corresponding to specific depths.
Figures 16A, 16B:
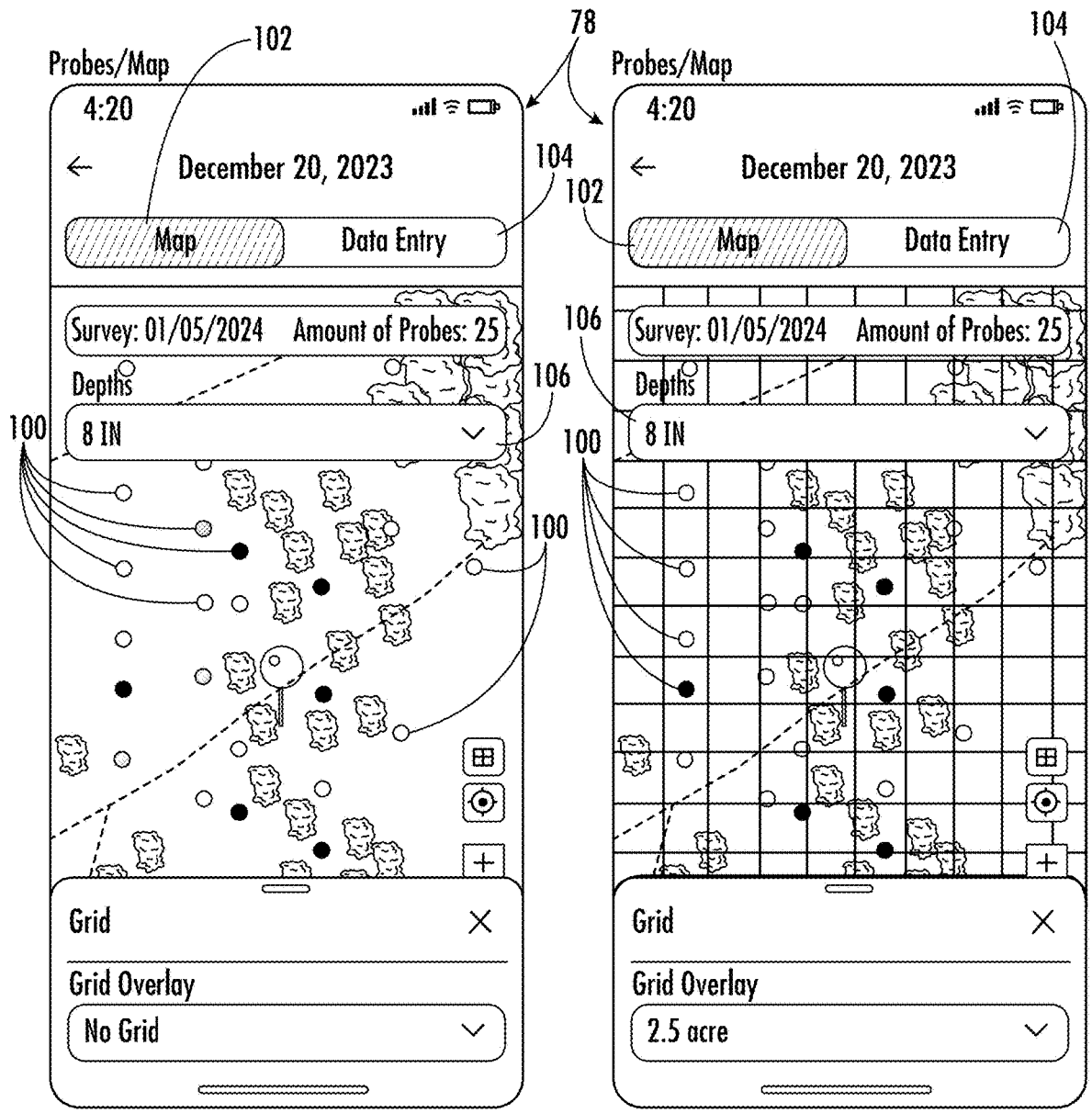
FIG. 16A is a graphical user interface of the map screen shown in FIG. 14 but with a grid overlay selection pop up present at the bottom of the graphical user interface according to an aspect of the present disclosure. An option is presented to the user to toggle a grid overlay on and off as well as adjust the size of the grid, where the grid overlay creates a grid of lines in a grid formation over the topographical map.
FIG. 16B is a graphical user interface of the map screen shown in FIG. 14 but with a grid overlay selection pop up present at the bottom of the graphical user and having the option for a grid overlay to be activated so that a grid is created over the topographical map interface according to an aspect of the present disclosure.

Whether the user selects an existing survey or creates a new one, they will be brought to a map screen 99. The map screen shows a satellite map generated of the area in which the survey was taken (FIGS. 14-16). Typically, the map is a top down view of the earth taken from a satellite and obtained from geographical information systems (GIS) software, such as GOOGLE EARTH PRO®, APPLE MAPS®, or ARC GIS®. The satellite image displayed is the most up to date version taken. For an existing survey, the map may the most updated version for when the survey was conducted, or it may still display the most up to date version for the current date in which the survey was accessed. The map screen shows the location of the user on the map or subsection of the map, as well as a number of soil compaction data entry points 100 corresponding to specific soil depths. The location of the user is marked with an icon or dot that is visually distinct from the background. The location of the user is also updated in real time so the user has an accurate understanding of where they are in their field and in relation to data entry points. The location icon of the user may be locked into the same location the map screen, so that the topographical map appears to move around in relation to the location of the user on the map screen 99. Alternatively, the map stays stationary, and the location of the user moves. The user may center the map on the user location at any time by selection of a button. The user may be able to change the view point of the map screen 99 and thus what part of the field is shown on the display of the mobile computing device. A user may change the view of the map by interacting with a touch display of the mobile computing device.

An existing survey will display a map screen having a plurality of data entry points 100 spread around it. The data entry points denote spots in the field where a user has used the penetrometer 10 to collect soil pressure data. The application stores data relating to the pressure at multiple depths into the soil associated with each of the data entry points. A user may view the pressure data for a particular data entry point by interacting with that data entry point 100. A pop up may appear that shows the depths and the pressure measurement collected at each. The survey screen also stores the information relating to the penetrometer used in the survey. The user will typically select the type of penetrometer they are using before they begin entering data entry points. The survey screen may also have multiple penetrometers stored if there were multiple types of penetrometers used or multiple users contributing to the survey with multiple penetrometers. The user may also select a particular depth to view. The selection may be done with a depth selection drop down menu, and will bring up a map for the selected depth and show data entry points associated with the selected depth. The user may select any data point and view the average pressure reading of each of the depth measurements at that point. Each data entry point displayed on the map will be associated with a particular measurement done in that spot at the selected depth. The data entry points will have a color that corresponds to the pressure measurement. The color may change at different depths, so a survey may have data entry points 100 that change their color between maps for each depth. The map may instead show only the average pressure value and color for each data entry point. This makes decision making and analysis easier because a farmer only has to look at a single map instead of multiple. Deciding to use a farming technique based on only a single map may lead to inaccuracies and suboptimal or harmful tillage or other soil treatments.

There are two tabs located above the main mapping screen, a view map tab 102, and a data entry tab 104. The view map tab displays the aforementioned satellite view of the field and the data entry points. A depth drop-down 106 menu below the view map tab 102 allows a user to view each of the data entry points at a specific depth with the appropriate color to indicate the compaction level. If a user selects four inches, they will be able to view the data entry points at four inches specifically. The data entry tab 104 will display the data entry screen 105 shown in FIG. 15B and set a data entry point at the user's location on the satellite map. The data entry screen 105 displays data entry fields 108 corresponding to specific depths. The number of data entry fields 108 corresponds to the number of notches 22 on the penetrometer 10 being used for the survey. If the penetrometer 10 has four notches 22, thus four measuring depths, then there should only be four data entry fields 108 for a user to fill. Typically, penetrometers have six to seven notches, so the application is able to accommodate seven or more data entry fields. The user takes their measurements, and inputs the measured value into the empty data entry fields using a standard mobile computing device keyboard. In a possible embodiment of the application, the user may also choose to lock in the value by selecting a keep value button located near to the data entry fields 108. Once the user is finished entering values, they may press an enter button, which saves the recorded data and closes the data entry screen and sends the user back to the map screen. If the user closes data entry screen 105 the data in the data entry fields 108 may be lost. The user types the measured pressure into the data entry point using the onscreen keyboard. The data entry screen 105 may be displayed adjacent to the satellite map in certain embodiments wherein the smart device is positioned in a landscape mode. Alternatively, the mobile application 78 may use the camera and visual character recognition to automatically record the data of the soil compaction readings and eliminate the manual data entry of this information or at least limit the manual data entry to verification of data autonomously read using the mobile application 78 and the systems for visualizing and processing the images provided by one or more of the mobile computing devices. The satellite image will also show the users location on the map corresponding to their location in real life in real time using a visually distinct location icon as they are collecting measurements. This way a user can go to a region of a field where a specific data point was taken to observe any changes in person. The average of all data points may be displayed for a particular field, which may also be displayed next to the link or map for that particular field, helping users to quickly determine the field's overall compaction level. The average value may also be shown in a CSV file with the raw compaction data. The collected field data is stored on the smart device memory, although it could be stored on a database external to the smart device or within a computer server in the cloud or otherwise stored in a remote location. The mobile computing device or the penetrometer can communicate with the server through a wireless internet or WIFI® connection. Selecting a data entry point "dot" or other geolocation on a satellite map of a given survey screen displayed to a user will display past testing data for that particular location for a given time the location was measured or potentially all data over time in aggregate to the user. This data may be filtered as well based on depth or other parameters as well.

Figure 17A:
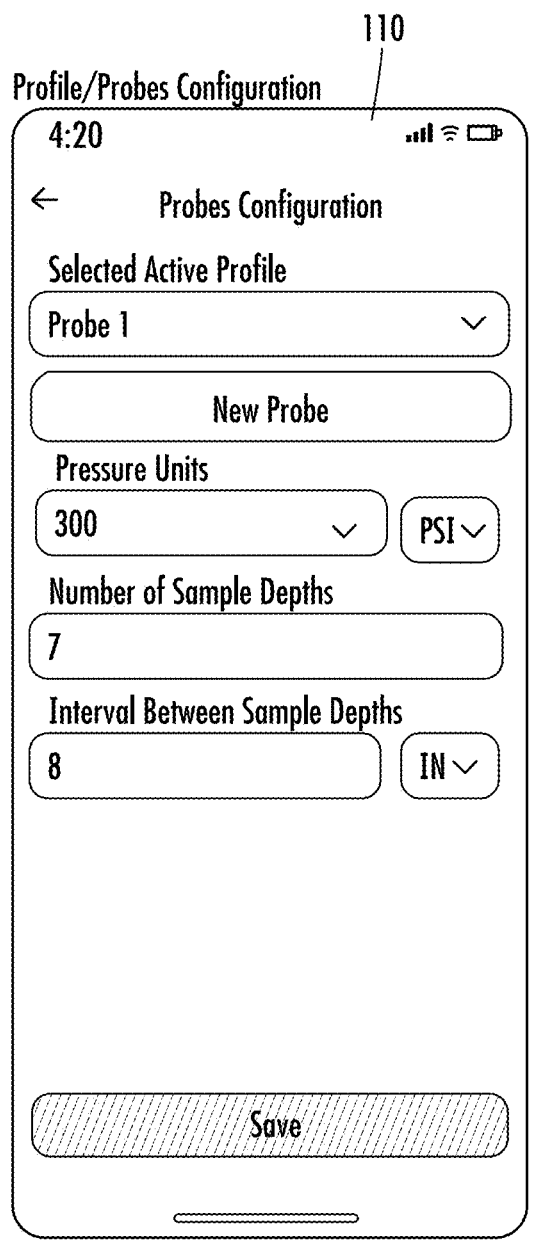
FIG. 17A is a graphical user interface of the probe configuration screen wherein a user can adjust the settings related to a particular penetrometer, such as the number of sample depths, notches, or pressure ranges available on the penetrometer according to an aspect of the present disclosure.
Figure 17B:
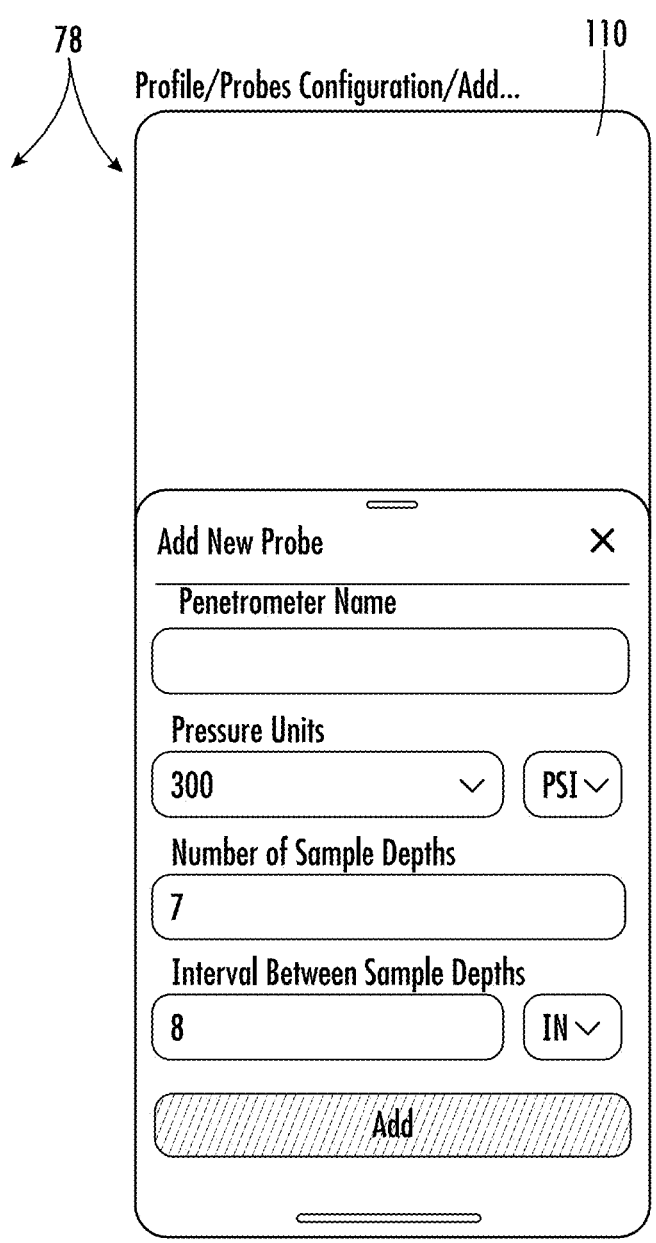
FIG. 17B is a graphical user interface of the add new probe screen wherein a user can set up settings for a particular penetrometer that may be different from other penetrometers saved in the mobile application according to an aspect of the present disclosure.

The application 78 further comprises a probe configuration screen 110 that is accessible to a user through their account. The user can use the probe configuration screen 110 to select from a number of penetrometer 10 configurations, possibly corresponding to known brands or models. A user may be prompted to select a particular brand and model stored within the application, and upon doing so, the application automatically creates a saved probe with the settings already made. A user may also enter custom values or edit an existing penetrometer 10 (FIG. 17A). The probe configuration can be set in relation to the number of samples/number of notches 22, interval between the notches 22, and the probe resolution. New probes can be added to and deleted from the application 78 (FIG. 17B), such as if the user purchases a new penetrometer 10, or makes modifications to an existing one. The penetrometer 10 settings are saved in the individual accounts so that a user may view and edit them while they are logged in. This also allows the user to have certain penetrometer 10 settings active regardless of what field and what organization 84 they have selected. A user may also select which penetrometer to use for different organizations. For example, a user could collect sample using penetrometer A for organization A, and collect sample using penetrometer B for organization B. Certain fields under a particular organization may also be tested with a different penetrometer as well. Perhaps an organization wants to collect measurements at field A every 3 inches, whereas field B and C only need to be measured every 4 inches.

The individual data points are color coded as a fast and easy way to convey soil density information to the user. The color is typically selected to be similar to the colors shown on the pressure gauge for different pressure/penetration resistance ranges. The pressure gauge 20 typically uses a standardized 0 to 300 psi range and displays green for a pressure range of 0-200 psi, yellow for 200-250 psi, orange 250-299 psi, and anything over 299 psi is red showing that there is likely to be significant crop yield loss due to compaction restricting root growth and action will need to be taken by the farmer to mitigate it. This reading assumes moderately saturated soil. The mobile application may adjust the color-coding scale for the moisture content of the soil if the soil is not moderately saturated, but this feature may not be employed. Alternatively, if the soil is not fully saturated, the color coding associated for a given data set may be adjusted based on moisture content of the soil, which adjusts the scaling based on the current estimated moisture content for the location/area. The color-coding range typically extends from 0 psi to about 900 psi as a typical range for a gauge on a digital penetrometer. An alternative penetrometer, which uses load cells, may have an unlimited scale, although they most commonly measure between 0 to 800 psi. The range of color from green to yellow is considered a good soil density. The colors shown are not just specifically red, green, and yellow. Data points can be shown in a gradient between green and yellow or yellow and red as well. This gives the user another way to visualize where on the density scale the soil falls without having to look deeper at the individual data points themselves. A point that is orange will represent soil that is not as dense as a red point but will be denser than a yellow point. This graduated visual representation is not necessary, but is typically preferred over just having the points set to only exact colors as it will skew the user's perception of the data collected. As discussed above, the color scaling can also be adjusted to reflect differences due to temperature and moisture content. The standardized soil pressure range of 0 to 300 psi is based on completely saturated soil and, as discussed, the systems of the present disclosure will not perfectly accurately measure the compaction of soil with a different moisture or temperature. For example, if soil is drier, it will appear to be more compacted. However, as discussed, the application can change the colors to show if the compaction level is still acceptable in the current conditions. The color scale may be shifted by changing its center point within the application or otherwise. Soil moisture data can be obtained through precipitation data, which may be collected from local weather data and possibly obtained from a publicly available weather database.

Alternatively, the color scale may be directly changed by the user. Instead of being presented with three options, corresponding to dry, moderately saturated, and fully saturated, the user may have a sliding scale that adjusts the colors according to their needs. The user may set dry to yellow, for example, and the other moisture levels are changed automatically or manually to compensate. The scale may be changed before a survey is taken, or at any point during or after the survey is taken. The color scale is not locked once a survey begins. A user may want to change the colors so that they may better understand the information or better present it to others. Different surveys may use different color scales as set by a user.

Rather than having a color scale based around a mid-point value shown on the pressure gauge, the colors are based off of the pressure values only. A yellow region would be 150 psi, for example, and not both the mid-point for a 0-900 psi gauge and 0-300 psi gauge. As such, values over a certain value, typically 400 psi, are typically colored the same. Red is the optimal color to represent the extreme values of compaction over 400 psi, representing areas needing the most tillage.

The application is able use interpolation to predict the compaction levels in areas of the field between measured data entry points. This allows the user to get an estimate for the entirety of their field without having to measure every square in of their field. The user can get accurate measurements using less time and man power, which is especially important if a field is being managed by a small number of people or even a single person. The systems of the present disclosure approximate the value of a potential new data entry point by comparing one or more data entry points around it. It then estimates the value for the potential point by linear interpolation, gaussian interpolations such as kriging, or other interpolation methods. The interpolation may be performed by the mobile computing device or penetrometer, or the calculations may be performed by the server after the measured data is communicated. The interpolation becomes more accurate as the number of data entry points increases. For example, if a user only takes a single data entry point, the system will not be able to compare it to any other are of the field, and the same values from the single data entry point may be assigned to any potential estimated data entry point. The interpolation is accurate enough to form a satisfactory soil tillage treatment prescription with relatively few data points. Ideally, accurate result may be obtained with less than one sample taken per acre. A user may create a new data point without physically measuring by selecting any region on the map screen and having the application perform calculations to assign the pressure values. The estimated pressure may be the estimated average pressure of each depth at a single point or a subset of the depths at a single point. A user may also view estimated values for a single depth. A user may also be able to enter a coordinate, and receive the estimated pressure values for the area of the field corresponding to the coordinate. Estimated values are assigned a color like the true measured values, and may also be gradients between those colors as well. The application may also suggest and identify additional geographical locations to take additional measurements to provide greater accuracy for the overall map using the interpolation systems.

The application may make use of artificial intelligence (AI) to calculate interpolated values as well as give feedback as to the accuracy of interpolated, measured, and average pressure values. For example, a subsection of a field may have a lot of variances in its pressure values, so interpolation may not be as accurate because there could be vastly different values located directly next to one another. The AI is able to detect the fluctuations and alert the user to perform additional measurements so that the accuracy of the interpolated points and true measured points can be better understood. The AI may make suggestions on precise locations in which to perform measurements as well as the number of measurements to make. As data is collected, the AI may update its suggestions in response to changes in data accuracy. The AI may also show a value corresponding to the level of accuracy for all or a subset of the measurements, or for any region of a field. The level of accuracy may be given in the form of a percentage, and may be accompanied by a color-coded system to communicate it better. 100% could be green for example. The AI may also show a user an expected increase in accuracy due to undertaking suggested actions. A measurement in a certain point in the field may increase the accuracy of the field measurements by 10%.

It is important to collect data and create maps for multiple different depths as the soil may have fluctuating densities only a short space apart. Only collecting readings for the top layer tells the user nothing about how the soil is further down, and as a result, a user may not realize that the crop growth could be affected by changes in the soil deeper below the surface. As an example, a particular data entry point may be green at 4 inches, orange at 8 inches, and red at 12 and below, indicating that the soil becomes more compacted the further down it goes. If a group of data points in a similar region are all having similar color profiles, then the soil density profile is likely similar throughout the region the data entry points were taken in. This is an indicator that the user may need specialized equipment to handle the problem rows/locations within the field to be tilled or amended.

To use the penetrometer 10 and its associated software application, the user will typically first collect data measurements. As shown in FIG. 2, the user holds the penetrometer 10 by the right side handle 18 and left side handle 16 and orients it as vertically as possible with the cone 24 directed downwards into the soil so that there are as little errors in measuring the depth as possible. The user presses the support rod 12 straight downward until the soil surface and the leveling plate 56 line up with the notch 22 that corresponds to the first desired depth measurement to be taken. The user opens the data entry screen in the application 78, which collects the coordinates of the ongoing measurement, and then the user inputs the pressure reading from the pressure gauge 20 into the correct data entry field in the data entry screen 105. This may be done manually or automatically by pressing a physical switch such as a thumb switch on the handle connected via a wireless signal such as a BLUETOOTH® or other connection or by activating a location on the touch screen of the mobile computing device to indicate to the device to record the reading on the pressure gauge.

After the data for the first depth has been inputted into the database of the present application, the user once again presses the support rod 12 into the soil until the surface and the leveling plate 56 line up with the next/subsequent desired depth, which is typically an equal increment of the first measurement, but can be different. The user repeats the recording procedure until data has been collected for each of the desired depths at each location within a field to be tested. When the user is finished with readings at a given location, they extract the support rod 12 out of the soil and move the penetrometer 10 to the next point of interest. The user then follows the measurement procedure used on the previous point again. The user takes readings at as many points as needed to get an accurate map of the soil density profile for their particular field. Typically, more locations in a given field yield better results for adjustment of how a farmer operates in their fields.

In the case that the smart device is equipped with enhanced photo detection software, the measurement process might be modified. In particular, the user positions the phone holder above the pressure gauge 20 of the penetrometer 10 such that the camera of the smart device can clearly view the pressure gauge 20. The user then pushes the penetrometer 10 downward into the soil at a constant rate of 1 inch per second to allow the camera of the smart device to accurately record the readings shown on the pressure gauge 20. The image recognition software captures the reading shown on the dial and transfers the data to the software application directly. The software application will then fill out the data entry fields corresponding to the measured depth with the captured pressure data. Alternatively, the user may press a button or section of the touch sensitive display on the mobile computing device to have the mobile computing device record the measurement on the dial with the camera. In this case, the user presses the penetrometer to the desired depth, clicks the button or display section, the data is automatically entered into the software application, and the user may continue inserting the penetrometer. The user may be presented with a timer on the screen of the mobile computing device that helps them time the rate of insertion.

As an example, a penetrometer 10 with a 24 inch long central support rod 12 would take 24 seconds in order to measure the entire depth range. Penetrometers are most commonly about 24 inches long, so they will need 24 seconds to be fully inserted into the soil. A visual cue may be displayed on the screen of the smart device to assist the user in maintaining a proper insertion speed. In this situation, data across the entire depth and/or at the predetermined depths might be recorded.

Multiple users may be able to view field data saved under a particular organization whose data they are authorized to view and access. The ability to allow plurality of different users to access data for the same field allows a user testing the soil compaction with the mobile computing device integrated with a penetrometer system to work in tandem with another user in a tractor or other farming vehicle who is tilling or treating the field to provide custom soil treatment to the field that minimizes over-tilling and soil erosion while adequately tilling compacted soil portions of the field for optimum planting and plant growth. A first user collects soil readings ahead of the second user. A second user is able to view a new reading made by the first user in real time and apply the proper tillage to the specific area. Here, collecting data and tilling can be done at the same time. Many users can take soil compaction readings at different locations within a field during the same timeframe using a plurality of the penetrometer systems of the present disclosure taking soil readings as a group and covering a large area together and completing soil measurements for the whole field in considerably less time. The multiple users accessing the same database using the mobile computing systems and applications of the present disclosure can quickly jointly work to create sufficient numbers of readings throughout the field or a given geographic area to complete a variable soil prescription. This can be done before or simultaneously with the tilling of the field so long as there are an adequate number of data readings for a given segment/surface area of the field prior to tilling beginning/occurring at any given location. Users may view recorded data in real time in order to perform other soil treatments as well. A user operating a vehicle may apply cover crops or soil treatment chemicals as directed.

The raw data collected may be available in the software application 78 in spreadsheet form. In such a configuration the data is typically organized by sample number or location on one axis and by the soil depth on a second axis, and displays the pressure reading at each depth of the sample location. An average of the data can be shown which can correspond to the average of pressures at a certain depth across all samples, or just the average pressure measurements across all depths or a grouping of different depths at a particular sample location.

A comma-separated value (csv) file containing all of the compaction data for a particular survey can be shared through the application 78 to be processed by other applications and systems from third parties or manually reviewed and analyzed by one or more users. Much like the data entry points, the compaction data in the csv file may be color coded to further indicate the compaction level. To share the data with other computing systems, while on the survey screen 98, the user of the mobile application 78 of the present disclosure can export a csv file and thereafter transmit the data to another system. The exporting may be done by selecting an option in a dropdown menu, or the user may swipe the screen of the mobile computing device 26 in order to bring up an exporting option. The transmission of the data or subset of the data taken and/or managed and processed by the mobile application 78 of the present disclosure and any storage system(s) associated therewith may be through any wired or wireless signal transmission system such as a cellular or WIFI® system. These files can then be imported into GIS software systems such as GOOGLE EARTH PRO®, QGIS® (an open-source cross-platform desktop geographic information system (GIS) application 78 that supports viewing, editing, printing, and analysis of geospatial data), or ARCGIS® or ARCGIS PRO®, which works in two dimensions and three-dimensions for cartography and visualization, and includes machine learning (ML). This allows for more sophisticated analysis outside the confines of the software application 78. Each sample has a number associated with it, and the corresponding data entry points on the map display can display this sample number to form a legend to easily navigate to specific points of interest to the user.

Figure 18:
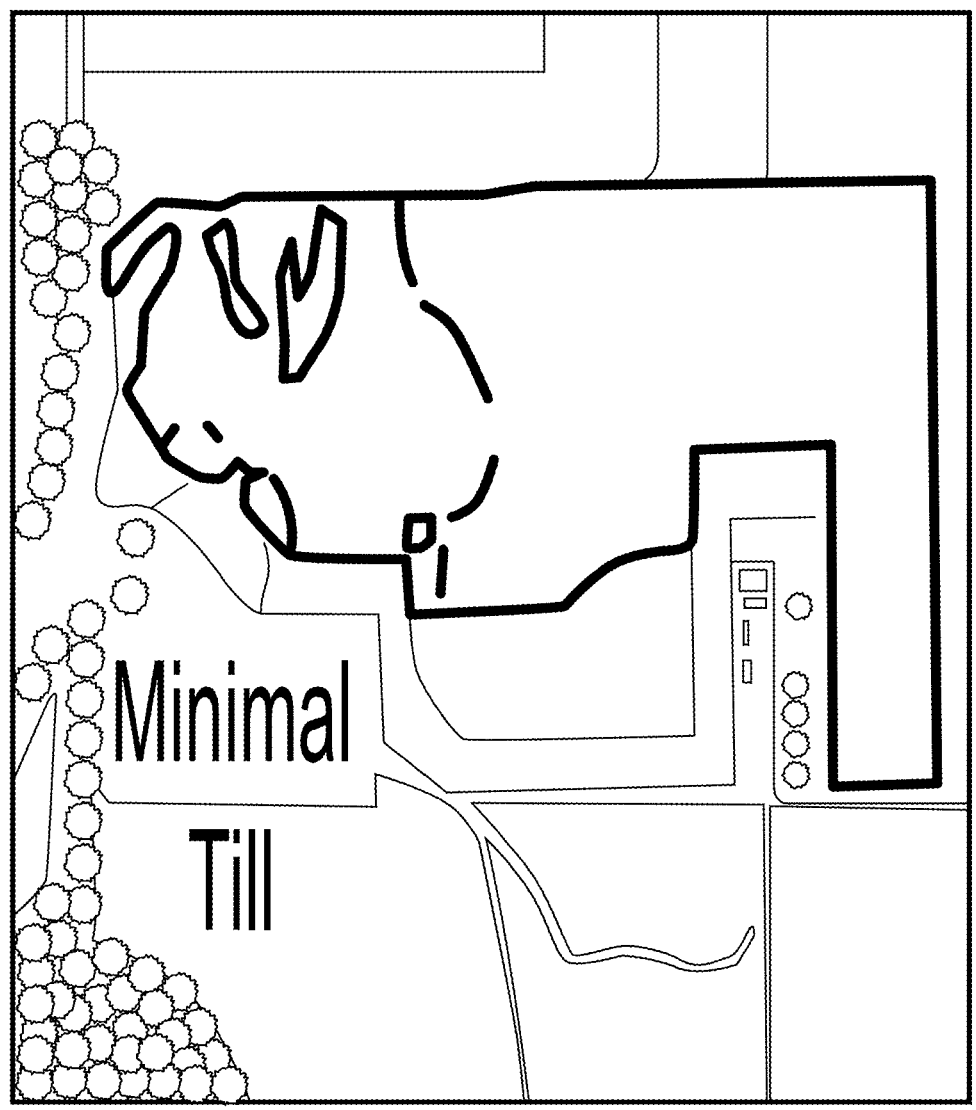
FIG. 18 is a graphical user interface showing a geographical map within the geographical location where penetrometer readings at various levels were taken and highlighting/suggesting to the user where specific tilling methods or farming methods according to a variable rate soil prescription that should be undertaken based on the readings at the various locations at the uniform depths across the map.

After the user collects their data and creates a soil density profile map using the systems and the mobile application 78 of the present disclosure, the user or users can formulate a variable rate soil prescription. FIG. 18 shows a possible soil prescription for a user to follow. The soil prescription provides the user with a graphical representation of automatic recommendations of how to till a given segment of the field analyzed, or whether to till at all, in every area/segment of the crop production field. A user may develop a soil prescription/plan manually through analysis of their collected data and experience, and/or they could create a shapefile to highlight specific regions of their field that need specific treatments. As discussed above, the geolocation of particular tillage levels needed may be integrated into or transmitted to a farming vehicle such as a tractor or a tilling implementing system consisting of a tractor and a tillage implement, which may be an automatic height adjusting cultivator. In such instances the farming vehicle will independently use the data to change the tilling based on the geographical location of the tillage implement and/or tractor while the field is being traversed. Users can more easily avoid common issues such as over tilling certain regions of their field, leading to permanent erosion damage. Another potential issue is the tendency of soil to become less compact and gain a more uniform density as it goes deeper. The prescription can indicate to the user that they should only till the top layers or that their current tilling method is responsible for the difference and should be corrected. The software application and the prescription can also help a user catch other issues such as lighter colored soils that are low on organic matter. Tilling soil that is low in organic matter will typically make the soil compaction levels worse, so the systems of the present disclosure may include a built-in way to detect areas with low organic matter and alert the user so that the user does not accidentally damage their soil quality. Satellite images may be visually examined with light soil typically being lower in organic matter than darker soil when imaged from space. The user can follow the soil prescription to adjust their farming practices and improve soil quality. A user may use various types of tillage, but they may also use other methods. A farmer can apply cover crops to reduce erosion as well as add helpful nutrients to the soil, inhibit weed growth, and other beneficial effects. In many cases, applying cover crops are better than tillage. The variable rate soil prescription helps identify what regions of a field to apply cover crops. A user may also apply different chemicals to the soil. For example, a farmer may use humic acid to improve soil structure and fertility.

The variable rate soil prescription or plans produced using the systems of the present disclosure can be tailored to the individual user. It will change field to field and is dependent on what specific tillage implement(s) and other farming equipment the user has access to. A possible implementation uses a tillage system that automatically adjusts its depth to account for the soil prescription. An exemplary system that might be used in conjunction with the penetrometer 10 systems of the present disclosure is the JOHN DEERE® TRUSET® system or any other systems that allows the tillage implements to be automatically adjusted, typically by automatically adjusting the depth, down-pressure, gang angle, basket down pressure, fore/aft and/or side-to-side tilt from the cab and on-the-go a matter of only a few seconds, typically six seconds or less. Such automatically and dynamically adjusting systems can accept the penetrometer 10 data and automatically raise and lower the tillage implements in use. The soil prescription/plan can change if the user does not own or could not obtain such an automatically implementing system to be used in conjunction with the penetrometer 10 systems of the present disclosure. Instead of using an automatically and dynamically adjustable tillage farm implement system, a user could alternatively implement a soil prescription or plan produced using the systems of the present disclosure by tilling and viewing a compaction map produced using the systems of the present disclosure on a mobile computing device 26 capable of visually displaying a geographical map of the soil prescription plan and a geolocation of the device and farm implement on the geographical map with the tillage plan displayed thereon. An example is shown in FIG. 9 using the monitor bar adapter 60. A variable rate soil prescription also typically includes consideration of soil texture, leftover residue from previous crops, and physical subsurface structure of the soil to be as accurate and useful as possible.

As discussed herein previously, accurate soil data will require accounting for the moisture of the soil as well as the soil type. Dryer soil will appear to be more compacted, for example. Sandy soils can appear to be more compacted because they are drier and well drained. Clays also appear to be highly compacted. The software application 78 will use the moisture profile while mapping. This way it will be able to more accurately portray the soil compaction gradients and better predict compaction in areas that have not been directly measured. Data on soil moisture levels can be obtained from public information automatically by the software application 78 or by manual activation within the mobile application 78 by the user or by exporting the data from the systems of the present disclosure to be processed by third party software. Soil moisture data may be obtained from sources such as the USDA Natural Resources Conservation Service (NCRS). Soil type data may be obtained public sources of information such as the US Geological Survey (USGS). Information from public sources may be overlaid onto compaction maps to further assist the user in understanding their field's soil structure. The soil saturation levels can then be input into the system, typically in the add survey screen 98 or the edit survey screen 98. Alternatively, the penetrometer 10 may include an onboard or separate moisture sensing means that transmits moisture data directly to the device on which the software app is running, either serially or wirelessly. This moisture information can also be simultaneously recorded along with the pressure data for adjustment of the pressure data in real-time or later. A user may instead enter moisture data manually.

Other factors that affect the readings of a penetrometer 10 include the temperature of the soil and the penetrometer 10 itself. The ground will typically freeze around 32° Fahrenheit, preventing a user from obtaining accurate results if the user attempts to measure soil data too early in the year or too late. If the user has an idea of the frost value of their field at a particular time, they can more accurately determine a soil prescription/plan in colder weather, even if they are collecting data at a colder time of year. A frost value estimate can be obtained from a publicly available database or reports. The software application 78 can alert the user directly if publicly available frost value estimate data is available for use and integration by the systems of the present disclosure. Alternatively, the air and/or soil temperature can be measured by a thermometer onboard the penetrometer 10 or on an external device. The data would then be transmitted serially or wirelessly, or possibly manually entered into the software application 78 by the user.

In another aspect of the present disclosure, the software application 78 may save historical data from a given field. This allows the user to compare a particular point in a field with the same or similarly located point from one or more previous years. A user can then judge whether the conditions in that section of field are getting worse or improving. If a user utilized a particular tillage method to try to improve a section of field, but the historical data shows no improvement or degradation, the user can determine if they need to change tactics or to be aware of other factors contributing to the decline. The user could also take pictures of these locations and save them to have a visual comparison to the section of field later.

What is claimed is:

1. A method for performing a soil compaction survey for a geographical area comprising the steps of:
    inserting a handheld penetrometer to a predetermined depth at a first point within the geographical area, wherein the handheld penetrometer is hand operated without the use of tools, and wherein the handheld penetrometer comprises:
        a downwardly extending support pole having a top portion with a top end, and a ground engaging end that is opposite from the top end on the downwardly extending support pole; an outwardly extending right side handle engaged to the downwardly extending support pole proximate the top portion;
        an outwardly extending left side handle engaged to the downwardly extending support pole proximate the top portion;
        a pressure gauge having a perimeter defining a pressure gauge perimeter shape wherein the pressure gauge has a pressure sensor system that detects a pressure exerted on the downwardly extending support pole and wherein the pressure exerted on the downwardly extending support pole is displayed on a top, user facing surface of the pressure gauge; and
        wherein the pressure gauge presents a level of compaction at any predetermined depth at a point within the geographical area as a pressure reading when the handheld penetrometer is inserted into ground;
    manually or automatically recording a pressure reading displayed by the pressure gauge of a first predetermined depth at the first point within the geographical area into a soil compaction mapping and tracking system of a computing system wherein the soil compaction mapping and tracking system displays a map of the geographical area and a location of a user of the handheld penetrometer on the map of the geographical area in real time on a touch sensitive display screen of a computing device, and wherein the pressure reading corresponds to a point on the map of the geographical area and configured to be viewed by one user or a plurality of additional users simultaneously using the soil compaction mapping and tracking system in real time by selection of the point on the map of the geographical area on the touch sensitive display screen of the computing device of a given user, and wherein the soil compaction mapping and tracking system is held on the computing device and the soil compaction mapping and tracking system is shown to a user on a screen of the computing device;
    inserting the handheld penetrometer to a second predetermined depth at the point within the geographical area;
    manually or automatically recording a pressure reading displayed by the pressure gauge of the second predetermined depth at the point within the geographical area into the soil compaction mapping and tracking system, and wherein the pressure reading corresponds to the point on the map of the geographical area and can be viewed by one or more users of the soil compaction mapping and tracking system in real time by selection of the point on the map of the geographical area;
    inserting the handheld penetrometer to an optional additional predetermined depth at the point within the geographical area;
    manually or automatically recording a pressure reading displayed by the pressure gauge of the optional additional predetermined depth at a point within the geographical area into the soil compaction mapping and tracking system, and wherein the pressure reading corresponds to the point on the map of the geographical area and can be viewed by the one or more users of the soil compaction mapping and tracking system in real time by selection of the point on the map of the geographical area.

2. The method of claim 1, wherein the step of manually or automatically recording a pressure reading displayed by the pressure gauge of a first predetermined depth at a point within the geographical area further comprises creating the point on the map of the geographical area by selection of a point activation link shown to a user on the screen of the computing device, and wherein the point on the map of the geographical area is created on the map of the geographical area corresponding to a location of the user of the handheld penetrometer in the geographical area in real time, and wherein a data entry system is displayed to the user of the handheld penetrometer upon selection of the point on the map of the geographical area and the data entry system has at least two data entry fields corresponding to at least two predetermined depths.

3. The method of claim 2, wherein the computing device is a user operated mobile computing device and the handheld penetrometer further comprises a mounting system for the removable attachment of the user operated mobile computing device such that the user operated mobile computing device is in line or the user operated mobile computing device is at least substantially in line with the downwardly extending central support pole and a display screen of the user operated mobile computing device is viewable while the handheld penetrometer is in use by the user of the handheld penetrometer, wherein the mounting system comprises:
    a gauge perimeter shape engaging clamping section where at least a majority of the gauge perimeter shape engaging clamping section has an overall shape that is the same shape or the gauge perimeter shape engaging clamping section has substantially the same shape as the pressure gauge perimeter shape and wherein the gauge perimeter shape engaging clamping section is frictionally held in engagement with the perimeter of the pressure gauge using a clamp or fastener such that the gauge perimeter shape engaging clamping section engages and conforms with the perimeter of the pressure gauge when engaged with the pressure gauge;

a user operated mobile computing device retention portion that releasably engages and disengages the user operated mobile computing device; and wherein the clamp or fastener is loosed or removed by hand and without the use of tools to disengage the mounting system from the perimeter of the pressure gauge when desired by the user.

4. The method of claim 2, wherein the computing device is integrated into the handheld penetrometer to form a penetrometer integrated computing device, and wherein the penetrometer integrated computing device comprises:

the pressure sensor system, wherein the pressure sensor system comprises a pressure sensor or a plurality of pressure sensors;

a processor;

a computer memory; and wherein the screen of the computing device is touch sensitive and touch activated, and wherein the handheld penetrometer includes a power supply, and wherein the computing device is attached to the power supply and receives power from the power supply.

5. The method of claim 1, wherein the pressure sensor system is chosen from the group consisting of a strain gauge, a piezoelectric sensor, a capacitive sensor, a fluid pressure sensor, or a pressure transducer.

6. The method of claim 1, wherein the pressure sensor system comprises a pressure sensor that is chosen from the group consisting of a strain gauge, a piezoelectric sensor, a capacitive sensor, a fluid pressure sensor, or a pressure transducer.

7. A method for performing a soil compaction survey for a geographical area to determine a level of compaction in at least one predetermined depth at a plurality of points within the geographical area, wherein the method comprises the steps of:

a) inserting a handheld penetrometer to a predetermined depth at a point within the geographical area, wherein the handheld penetrometer is hand operated without the use of tools, and wherein the handheld penetrometer comprises:

a downwardly extending central support pole having a top portion with a top end, and a ground engaging end that is opposite from the top end on the downwardly extending support pole;

an outwardly extending right side handle engaged to the downwardly extending support pole;

an outwardly extending left side handle engaged to the downwardly extending support pole;

a pressure gauge having a perimeter defining a gauge perimeter shape wherein the pressure gauge has a pressure sensor system that detects a pressure exerted on the downwardly extending support pole and wherein the pressure exerted on the downwardly extending support pole is displayed on a top, user facing surface of the pressure gauge;

and wherein the pressure gauge presents a level of compaction at the predetermined depth at a point within the geographical area as a pressure reading;

b) manually or automatically recording a pressure reading displayed by the pressure gauge of a first predetermined depth at the point within the geographical area into a soil compaction mapping and tracking system wherein the soil compaction mapping and tracking system displays a map of the geographical area and a location of a user of the handheld penetrometer on the map of the geographical area in real time, and wherein the pressure reading corresponds to a point on the map of the geographical area and can be viewed by one or more users of the soil compaction mapping and tracking system in real time by selection of the point on the map of the geographical area, and wherein the soil compaction mapping and tracking system is held on a computing device;

c) optionally inserting the handheld penetrometer to an optional additional predetermined depth at the point within the geographical area;

d) optionally manually or automatically recording a pressure reading displayed by the pressure gauge of the optional additional predetermined depth at a point within the geographical area into the soil compaction mapping and tracking system, and wherein the pressure reading corresponds to the point on the map of the geographical area and can be viewed by the one or more users of the soil compaction mapping and tracking system in real time by selection of the point on the map of the geographical area;

e) optionally repeating steps c-d for any number of additional optional predetermined depths at the point within the geographical area;

f) moving the handheld penetrometer to a subsequent point within the geographical area; and g) repeating steps a-f for any number of subsequent points within the geographical area.

8. The method of claim 7, wherein the step of manually or automatically recording a pressure reading displayed by the pressure gauge of a first predetermined depth at a point within the geographical area further comprises creating the point on the map of the geographical area by selection of a point activation link shown to a user on a screen of the computing device, and wherein the point on the map of the geographical area is created on the map of the geographical area corresponding to a location of the user of the handheld penetrometer in the geographical area in real time, and wherein a data entry system is displayed to the user of the handheld penetrometer upon selection of the point on the map of the geographical area and the data entry system has at least one data entry field corresponding to the at least one predetermined depth.

9. The method of claim 8, wherein the computing device is a user operated mobile computing device and the handheld penetrometer further comprises a mounting system for the removable attachment of the user operated mobile computing device such that the user operated mobile computing device is in line or at least substantially in line with the downwardly extending central support pole and a display screen of the user operated mobile computing device is viewable while the handheld penetrometer is in use by the user of the handheld penetrometer, wherein the mounting system comprises:

a gauge perimeter shape engaging clamping section where at least a majority of the gauge perimeter shape engaging clamping section has an overall shape that is the same shape as the gauge perimeter shape and is frictionally held in engagement with the perimeter of the pressure gauge using a clamp or fastener such that the gauge perimeter shape engaging clamping section engages and conforms with the perimeter of the pressure gauge when engaged with the pressure gauge;

a user operated mobile computing device retention portion that releasably engages and disengages the user operated mobile computing device; and wherein the clamp or fastener is loosed or removed by hand and without the use of tools to disengage the mounting system from the perimeter of the pressure gauge when desired by the user.

10. The method of claim 8, wherein the computing device is a penetrometer integrated computing device, and wherein the penetrometer integrated computing device comprises:

a processor;

a computer memory; and wherein the screen of the computing device is touch sensitive and touch activated, and wherein the handheld penetrometer includes a power supply, and wherein the computing device is attached to the power supply and receives power from the power supply.

11. The method of claim 8, wherein the computing device is a user operated mobile computing device and the handheld penetrometer further comprises a mounting system for the removable attachment of the user operated mobile computing device such that the user operated mobile computing device is in line or at least substantially in line with the downwardly extending central support pole and a display screen of the user operated mobile computing device is viewable while the handheld penetrometer is in use by the user of the handheld penetrometer, wherein the mounting system comprises a user operated mobile computing device retention portion that releasably engages and disengages the user operated mobile computing device and wherein the user operated mobile computing device retention portion is permanently affixed to the handheld penetrometer and cannot be removed by hand or without the use of tools.

12. The method of claim 8, wherein the handheld penetrometer further comprises a plurality of horizontal notches on the downwardly extending central support pole that are evenly spaced and parallel with one another and that correspond to the at least one predetermined depth of the handheld penetrometer while it is inserted into the ground, and wherein an amount of horizontal notches corresponds to an amount of data entry fields within the data entry system.

13. The method of claim 12, wherein the handheld penetrometer further comprising a leveling plate spaced around the downwardly extending central support pole wherein the leveling plate is planar and has a hole located substantially in its center, and wherein the hole has a diameter that is greater than a diameter of the downwardly extending central support pole, and wherein the leveling plate fits over the downwardly extending central support pole and slides up and down the downwardly extending central support pole due to a force of gravity but without falling off or being removed by gravity alone, and wherein the at least one predetermined depth is found by aligning the leveling plate and a horizontal notch with one another and aligning the horizontal notch and the leveling plate with a surface of soil at the point within the geographical area.

14. The method of claim 7, wherein the plurality of points of the geographical area is in an amount less than one point per acre of the geographical area.

15. The method of claim 7, further comprising a step of creating one or more estimated points on the map of the geographical area having at least one automatically estimated pressure value corresponding to a predetermined depth, wherein the step comprises a user of the soil compaction mapping and tracking system selecting an area of the map of the geographical area without an estimated point or a point of the geographical area obtained from measurements taken with the handheld penetrometer, and the soil compaction mapping and tracking system calculating an estimated pressure value by interpolation.

16. The method of claim 7, further comprising the steps of:

using collected points of the map of the geographical area having pressure values to construct a soil treatment prescription with different levels of soil treatment based on levels of compaction present at each point of the geographical area; and using the soil treatment prescription for the geographical area to change soil treatment of the geographic area based on the soil treatment prescription created using the collected points of the map of the geographical area having pressure values.

17. The method of claim 16, wherein the soil treatment prescription is provided to a cultivator, and if the soil treatment prescription indicates a level of tillage, then the cultivator automatically adjusts the level of tillage based on the level of tillage of the soil treatment prescription.

18. The method of claim 7, wherein the soil compaction mapping and tracking system is accessed by the computing device and one or more additional computing devices simultaneously, and wherein the map of the geographical area is displayed on a display of each of the one or more additional computing devices and is updated in real time when a user of the soil compaction mapping and tracking system changes the map of the geographical area.

19. A method for performing a soil compaction survey for a geographical area to determine a level of compaction in at least one depth at a plurality of points within the geographical area, wherein the method comprises the steps of:

a) inserting a handheld penetrometer at a constant rate into a point within the geographical area, wherein the handheld penetrometer is hand operated without the use of tools, and wherein the handheld penetrometer comprises:

a downwardly extending support pole having a top portion with a top end, and a ground engaging end that is opposite from the top end on the downwardly extending support pole;

an outwardly extending right side handle engaged to the downwardly extending support pole;

an outwardly extending left side handle engaged to the downwardly extending support pole;

a pressure gauge having a perimeter defining a gauge perimeter shape wherein the pressure gauge has a pressure sensor system that detects a pressure exerted on the downwardly extending support pole and wherein the pressure exerted on the downwardly extending support pole is displayed on a top, user facing surface of the pressure gauge;

and wherein the pressure gauge presents a level of compaction at a predetermined depth at a point within the geographical area as a pressure reading;

b) automatically, without data entry by a user of the handheld penetrometer, recording a pressure reading displayed by the pressure gauge of a first predetermined depth at the point within the geographical area into a soil compaction mapping and tracking system using a user operated mobile computing device wherein the soil compaction mapping and tracking system displays a map of the geographical area and a location of a user of the handheld penetrometer on the map of the geographical area in real time, and wherein the pressure reading corresponds to a point on the map of the geographical area and can be viewed by one or more users of the soil compaction mapping and tracking system in real time by selection of the point on the map of the geographical area, and wherein the soil compaction mapping and tracking system is held on the user operated mobile computing device;

c) optionally inserting the handheld penetrometer to any number of additional optional depths at a constant rate;

d) automatically, without data entry by a user of the handheld penetrometer, recording a pressure reading displayed by the pressure gauge of the any number of optional additional predetermined depth at a point within the geographical area into the soil compaction mapping and tracking system, and wherein the pressure reading corresponds to the point on the map of the geographical area and can be viewed by the one or more users of the soil compaction mapping and tracking system in real time by selection of the point on the map of the geographical area;

e) moving the handheld penetrometer to a subsequent point within the geographical area; and f) repeating steps a-e for any number of subsequent points within the geographical area.

20. The method of claim 19, wherein the pressure reading is automatically recorded by a camera of the user operated mobile computing device and the pressure reading is entered into data entry fields associated with the point on the map of the geographical area by the soil compaction mapping and tracking system.

* * * * *